(12) United States Patent
Greener et al.

(10) Patent No.: US 11,564,844 B2
(45) Date of Patent: Jan. 31, 2023

(54) REDUCED PRESSURE THERAPY SYSTEMS AND METHODS FOR MONITORING PATIENT MOVEMENT

(71) Applicant: T.J.Smith and Nephew, Limited, Hull (GB)

(72) Inventors: Bryan Greener, York (GB); Edward Yerbury Hartwell, Hull (GB); Felix Clarence Quintanar, Hull (GB)

(73) Assignee: T.J.Smith and Nephew, Limited, Hull (GB)

(\*) Notice: Subject to any disclaimer, the term of this patent is extended or adjusted under 35 U.S.C. 154(b) by 925 days.

(21) Appl. No.: 16/326,162

(22) PCT Filed: Aug. 18, 2017

(86) PCT No.: PCT/IB2017/001162
§ 371 (c)(1),
(2) Date: Feb. 15, 2019

(87) PCT Pub. No.: WO2018/033794
PCT Pub. Date: Feb. 22, 2018

(65) Prior Publication Data
US 2019/0192744 A1 Jun. 27, 2019

Related U.S. Application Data

(60) Provisional application No. 62/423,441, filed on Nov. 17, 2016, provisional application No. 62/377,418, filed on Aug. 19, 2016.

(51) Int. Cl.
*A61F 13/00* (2006.01)
*A61F 13/02* (2006.01)
*A61M 1/00* (2006.01)

(52) U.S. Cl.
CPC .... *A61F 13/00068* (2013.01); *A61F 13/0216* (2013.01); *A61M 1/73* (2021.05);
(Continued)

(58) Field of Classification Search
CPC ......... A61B 5/103; A61B 5/1123; A61B 5/11; A61B 5/00; A61B 5/4483; A61M 5/11;
(Continued)

(56) References Cited

U.S. PATENT DOCUMENTS 7,378,975 B1\* 5/2008 Smith .................. A61B 5/1126
7,569,742 B2 8/2009 Haggstrom et al.
(Continued)

FOREIGN PATENT DOCUMENTS

CN 202568632 U 12/2012
WO WO-2004060148 A2 \* 7/2004 .......... A61M 1/0031
(Continued)

OTHER PUBLICATIONS

Cheatham, Micheal L. Negative Pressure Wound Therapy. Orlando Regional Medical Center, Feb. 14, 2015 [online], [retrieved on Nov. 30, 2021]. Retrieved from the internet: <URL: http://surgicalcriticalcare.net/Guidelines/NPWT%202014.pdf>.\*
(Continued)

*Primary Examiner* — Erich G Herbermann
*Assistant Examiner* — Linnae E. Raymond
(74) *Attorney, Agent, or Firm* — Knobbe, Martens, Olson & Bear, LLP

(57) ABSTRACT

According to certain embodiments, an apparatus for applying negative pressure to a wound can include a negative pressure source, a sensor, and a controller. The negative pressure source can be configured to couple via a fluid flow path to a wound dressing and provide negative pressure to the wound dressing. The sensor can be configured to monitor a magnitude or frequency of pressure in the fluid flow path
(Continued)

generated by the negative pressure source. The controller can be configured to determine an activity classification, such as breathing, changing positions while lying, sitting, walking, standing, jumping, traversing stairs, leg extending, leg bending, and performing chair squats, based on a change in the magnitude of pressure over time while the negative pressure source maintains the magnitude of pressure in the fluid flow path below a negative pressure threshold. The controller can output an indication of the activity classification.

21 Claims, 24 Drawing Sheets

(52) U.S. Cl.
CPC .............. *A61M 1/917* (2021.05); *A61M 1/96* (2021.05); *A61M 2205/3584* (2013.01); *A61M 2205/502* (2013.01); *A61M 2205/52* (2013.01); *A61M 2230/06* (2013.01); *A61M 2230/42* (2013.01); *A61M 2230/62* (2013.01); *A61M 2230/63* (2013.01)

(58) Field of Classification Search
CPC .... A61M 1/90–985; A61M 1/71; A61M 1/74; A61M 1/00–985; A61N 1/36
See application file for complete search history.

(56) References Cited

U.S. PATENT DOCUMENTS

| | | | |
|---|---|---|---|
| 7,794,450 B2 | 9/2010 | Blott et al. | |
| 8,419,660 B1 * | 4/2013 | Shaw | A61B 5/6892 600/595 |
| 8,734,425 B2 | 5/2014 | Nicolini | |
| 9,168,179 B2 | 10/2015 | Robinson et al. | |
| 10,076,594 B2 | 9/2018 | Collinson et al. | |
| 10,155,070 B2 | 12/2018 | Childress et al. | |
| 2009/0209830 A1 * | 8/2009 | Nagle | A43B 7/147 |
| 2012/0283581 A1 * | 11/2012 | Oide | A61M 1/3639 600/485 |
| 2013/0085462 A1 * | 4/2013 | Nip | A61F 13/00068 604/315 |
| 2016/0206478 A1 | 7/2016 | Nordbo et al. | |
| 2017/0188946 A1 * | 7/2017 | Klusmann | G01P 1/023 |

FOREIGN PATENT DOCUMENTS

| | | | | |
|---|---|---|---|---|
| WO | WO-2009089390 A2 * | 7/2009 | .......... | A61M 1/0027 |
| WO | WO-2010111363 A2 * | 9/2010 | ............ | A61B 5/742 |
| WO | WO-2011008175 A1 * | 1/2011 | ........... | A61B 5/6887 |
| WO | WO-2012078724 A1 * | 6/2012 | ........... | A61M 1/0031 |
| WO | WO-2014066714 A1 * | 5/2014 | ........... | A61B 5/0053 |
| WO | WO 2015/023515 | 2/2015 | | |
| WO | WO-2015023515 A1 | 2/2015 | | |
| WO | WO-2016018448 A1 * | 2/2016 | .............. | A61M 1/74 |
| WO | WO 2017/087157 | 5/2017 | | |
| WO | WO-2017087157 A1 * | 5/2017 | ........... | A61B 5/1118 |
| WO | WO-2017197357 A1 | 11/2017 | | |
| WO | WO 2018/033794 | 2/2018 | | |
| WO | WO-2018231874 A1 | 12/2018 | | |
| WO | WO-2018231878 A1 | 12/2018 | | |

OTHER PUBLICATIONS

Renasys GO Negative Pressure Wound Therapy. Datasheet [online]. Smith & Nephew, 2015 [retrieved on Dec. 2, 2021]. Retrieved from the internet: <URL: https://www.smith-nephew.com/global/npwt%20revised%20instructions/renasys%20go%20user%20manual%20(66801244,%2066801496)_part1.pdf>.*
International Search Report and Written Opinion, re PCT Application No. PCT/IB2017/001162, dated Nov. 23, 2017.
International Preliminary Report on Patentability for Application No. PCT/IB2017/001162, dated Feb. 28, 2019, 7 pages.
International Search Report and Written Opinion for Application No. PCT/IB2017/001162, dated Nov. 23, 2017, 8 pages.

* cited by examiner

REDUCED PRESSURE THERAPY SYSTEMS AND METHODS FOR MONITORING PATIENT MOVEMENT

CROSS-REFERENCE TO RELATED APPLICATIONS

This application is claims the benefit of International Patent Application No. PCT/IB2017/001162, filed Aug. 18, 2017, entitled "Reduced Pressure Therapy Systems and Methods for Monitoring Patient Movement," which claims priority benefit to U.S. Provisional Application No. 62/377,418, filed Aug. 19, 2016, entitled "Systems And Methods For Applying Reduced Pressure Therapy," and U.S. Provisional Application No. 62/423,441, filed Nov. 17, 2016, entitled "Systems And Methods For Applying Reduced Pressure Therapy," each of which is incorporated herein in its entirety for all purposes.

FIELD

Embodiments of the present disclosure relate to apparatuses, systems, and methods for the treatment of wounds, for example using dressings in combination with negative pressure wound therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

BACKGROUND

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

However, prior art dressings for use in negative pressure wound therapy or other wound therapy provide little visualization or information of the condition of the wound site beneath the dressing. This can require the dressing to be changed prematurely before the desired level of wound healing has occurred or, for absorbent dressings, prior to the full absorbent capacity of the dressing being reached to allow the clinician to inspect the healing and status of the wound. Some current dressings have limited or unsatisfactory methods or features of providing information of conditions of the wound.

SUMMARY

Generally described, embodiments of the present disclosure are directed to a system, method, or apparatus for monitoring the movement of a patient with a negative pressure therapy apparatus. According to some embodiments, an apparatus for applying negative pressure to a wound can include a negative pressure source. The negative pressure source can be configured to couple to a wound dressing via a fluid flow path and further configured to provide negative pressure to the wound dressing. The apparatus for applying negative pressure can further include a sensor and a controller. The sensor can be configured to monitor a magnitude or frequency of pressure in the fluid flow path generated by the negative pressure source. The controller can be configured to determine an activity classification based on a change in the magnitude or frequency of pressure over time and output an indication of the activity classification. The negative pressure source can be configured to maintain the magnitude of pressure such that it satisfies a negative pressure threshold. In some instances, the activity classification can be indicative of a type of activity engaged in by an individual while wearing the wound dressing.

The apparatus of the preceding paragraph may also include any combination of the following features described in this paragraph, among others described herein. The activity classification can be one or more of breathing, changing positions while lying, sitting, walking, standing, jumping, traversing stairs, leg extending, leg bending, and performing chair squats. The wound dressing can be configured to be positioned on a knee, a heel, an elbow, a shoulder, a hip, a torso, or an abdomen of the individual. In some embodiments the apparatus can further include a user interface configured to receive the assigned classification as a user input to the user interface or output the indication of the activity classification for presentation.

The apparatus of any of the preceding paragraphs may also include any combination of the following features described in this paragraph, among others described herein. According to some embodiments, the controller is further configured to compare the activity classification to an assigned classification associated with the individual and output an indication of whether the activity classification matches the assigned classification. The controller can be further configured to wirelessly output the indication of the activity classification for presentation on a display screen to the individual. The controller can be further configured to transmit the indication of the activity classification to a computing device via a communication network. The controller can be further configured to store, in a memory device, the indication of the activity classification in association with usage data reflecting usage of the negative pressure source during a corresponding time period. According to some embodiments, the controller is further configured to monitor the pressure at the wound dressing, in one or lumens of the fluid flow path, or at an inlet of the negative pressure source.

The apparatus of any of the preceding paragraphs may also include any combination of the following features described in this paragraph, among others described herein. According to some embodiments, the activity classification is responsive to the change in the magnitude of pressure over a duration of at least 1 second, 10 seconds, 30 seconds, 1 minute, or 5 minutes. According to some embodiments, the activity classification is configured to be stored in a memory device. According to some embodiments, the fluid flow path comprises at least one lumen or a plurality of lumens. In some embodiments, the apparatus further comprises a canister configured to be in fluidic communication with the wound dressing and the negative pressure source via the fluid flow path, the canister being configured to collect exudate aspirated from a wound.

The apparatus of any of the preceding paragraphs may also include any combination of the following features described in this paragraph, among others described herein.

According to some embodiments, the controller is further configured to activate or deactivate the negative pressure source in response to the activity classification matching the assigned classification. The controller can be further configured to output an indication that the individual is changing positions while lying in response to the change in the magnitude of pressure satisfying a threshold pressure change. The negative pressure source can be configured to perform negative pressure therapy when the magnitude of pressure is maintained below the negative pressure threshold.

The apparatus of any of the preceding paragraphs may also include any combination of the following features described in this paragraph, among others described herein. According to some embodiments, the threshold pressure change is about 5 mmHg when the dressing is configured to be positioned on the heel, the threshold pressure change is about 6 mmHg when the dressing is configured to be positioned on the hip, and the threshold pressure change is about 10 mmHg when the dressing is configured to be positioned on the shoulder. The controller can be further configured to detect a duration of time during which the individual has not changed positions while lying and output another indication in response to the detected duration satisfying a threshold duration. The indication that the individual has not changed positions can be associated with at least one of development of a pressure ulcer, development of an injury, or loss of consciousness. The controller can be further configured to determine and provide indication of breathing when the dressing is applied to the torso or further configured to detect and provide indication of at least one of a heart rate or a pulse rate based on the change in the magnitude of pressure over time. The controller can be further configured to determine the activity classification based on a peak-to-peak change in the magnitude of pressure over time According to some embodiments, a method of operating a negative pressure wound therapy apparatus includes operating a negative pressure source fluidically coupled via a fluid flow path to a wound dressing positioned over a wound of a patient and monitoring, via a sensor, a magnitude of pressure in a fluid flow path. The method further includes determining an activity classification based on a change in the magnitude of pressure over time while the negative pressure source maintains the magnitude of pressure in the fluid flow path below a negative pressure threshold. The activity classification is indicative of a type of activity engaged in by the patient while wearing the wound dressing. The method further includes outputting an indication of the activity classification.

The method of the preceding paragraph may also include any combination of the following features or steps described in this paragraph, among others described herein. According to some embodiments, the activity classification is one or more of breathing, changing positions while lying, sitting, walking, standing, jumping, traversing stairs, leg extending, leg bending, and performing chair squats. The wound dressing can be positioned on a knee, a heel, an elbow, a shoulder, a hip, a torso, or an abdomen of the individual. The method can further include comparing the activity classification to an assigned classification associated with the patient, and outputting an indication of whether the activity classification matches the assigned classification. The method can further include further comprising receiving the assigned classification as a user input to the user interface. The method can further include outputting the indication of the activity classification for presentation. The method can further include wirelessly outputting the indication of the activity classification for presentation on a display screen to the patient.

The method of any of the preceding paragraphs may also include any combination of the following features or steps described in this paragraph, among others described herein. According to some embodiments, the activity classification is responsive to the change in the magnitude of pressure over a duration of at least 1 second, 10 seconds, 30 seconds, 1 minute, or 5 minutes. The method can further include storing the activity classification in a memory device. The method can further include transmitting the indication of the activity classification to a computing device via a communication network. The method can further include storing, in a memory device, the indication of the activity classification in association with usage data reflecting usage of the negative pressure source during a corresponding time period.

The method of any of the preceding paragraphs may also include any combination of the following features or steps described in this paragraph, among others described herein. According to some embodiments, the fluid flow path comprises at least one lumen or a plurality of lumens. The method can further include monitoring the pressure at the wound dressing, in one or lumens of the fluid flow path, or at an inlet of the negative pressure source. The method can further include collecting exudate aspirated from the wound in a canister in fluidic communication with the wound dressing and the negative pressure source via the fluid flow path. The method can further include activating or deactivating the negative pressure source in response to the activity classification matching the assigned classification. The method can further include performing negative pressure therapy when the magnitude of pressure is maintained below the negative pressure threshold. The method can further include outputting an indication that the patient is changing positions while lying in response to the change in the magnitude of pressure satisfying a threshold pressure change.

The method of any of the preceding paragraphs may also include any combination of the following features or steps described in this paragraph, among others described herein. According to some embodiments, the threshold pressure change is about 5 mmHg when the dressing is positioned on the heel, the threshold pressure change is about 6 mmHg when the dressing is positioned on the hip, and the threshold pressure change is about 10 mmHg when the dressing is positioned on the shoulder. The method can further include detecting a duration of time during which the patient has not changed positions while lying, and outputting another indication in response to the detected duration satisfying a threshold duration. In some embodiments, the indication that the individual has not changed positions is associated with at least one of development of a pressure ulcer, development of an injury, or loss of consciousness. The method can further include determining and providing indication of a breathing rate when the dressing is applied to the torso. The method can further include detecting and providing indication of at least one of a heart rate or a pulse rate based on the change in the magnitude of pressure over time. The method can further include determining the activity classification based on a peak-to-peak change in the magnitude of pressure over time.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which.

DETAILED DESCRIPTION

Overview

Figure 1:
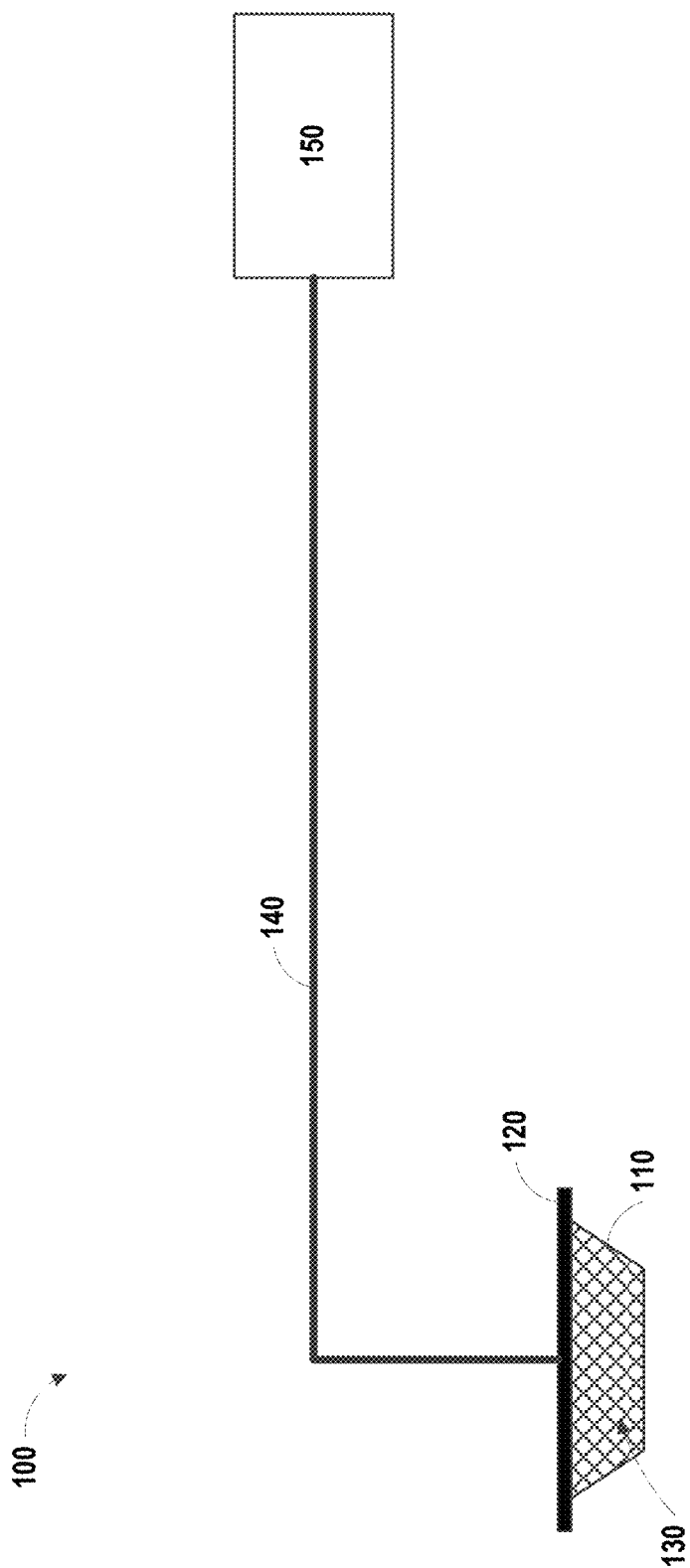
FIG. 1 illustrates a negative pressure wound therapy system according to some embodiments.

In some embodiments, a TNP apparatus can be used to monitor the movement or physiological characteristics of a patient. The TNP apparatus can, for example, analyze a magnitude (e.g., amplitude, peak-to-peak, peak-to-trough, etc.) or frequency of pressure pulses in a TNP system to characterize, track, and report types of movement by the patient. Different types of movement by the patient can result in different variations in the magnitude or frequency pressure over time, and the different variations can be indicative of particular movements by the patient. Similarly, different variations in the magnitude or frequency of pressure over time can also be used to calculate, estimate or monitor physiological characteristics of a patient.

A wound dressing (for example, such as one of the wound dressings described in U.S. application Ser. No. 14/715,527 (hereinafter "the '527 Application"), entitled Fluidic Connector for Negative Pressure Wound Therapy and published as US2016/0339158, which is incorporated by reference herein in its entirety) can be positioned on a patient (such as on a patient's knee, elbow, heel, shoulder, hip, torso or abdomen) and connected to a negative pressure source of a TNP apparatus so that such a TNP system achieves a relatively low pressure leak rate when negative pressure is maintained by the TNP apparatus. The leak rate can be sufficiently low (for example, about 10, 20, 30, 50, 75, 100, 150, 200, 250, 300, 400, 500, 750, or 1000 ml per day) that the negative pressure source of the TNP apparatus may, for at least some periods of time, provide negative pressure less frequently than every 30 seconds, 1 minute, 5 minutes, 10 minutes, 20 minutes, 30 minutes, 45 minutes, 60 minutes, 75 minutes, 90 minutes, 120 minutes, 150 minutes, 180 minutes, 210 minutes, or 240 minutes, and yet negative pressure can be maintained by the TNP apparatus under the wound dressing at a level sufficient to provide negative wound pressure therapy. The variations in a magnitude or frequency of pressure over time in the TNP system with such low leak rates can be desirably indicative of variations in a physical area within which negative pressure is maintained by the TNP apparatus and thus be used to infer patient movements (for example, knee bending, walking, breathing, exercising, sleeping, moving to prevent pressure injury like pressure ulcers, standing, jumping, traversing stairs, leg extending, and performing chair squats) or physiological characteristics (for example, breathing rate, pulse, and heart rate).

Patient ambulation and mobility may be recommended within 24 hours of a knee, hip, or caesarean surgery. Following a knee, hip, or caesarean surgery, a TNP apparatus can accordingly advantageously, in certain embodiments, be used to monitor patient recovery, such as remotely and after a patient has returned home for in-home recovery. The TNP apparatus can monitor activity, determine compliance with an exercise regimen (such as to improve an operated knee), and provide feedback to a patient or clinician (such as to output data to multiple individuals involved in the rehabilitating the patient).

Embodiments disclosed herein relate to apparatuses and methods of treating and/or monitoring a wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sternotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Embodiments disclosed herein relate to systems and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure ("TNP") or reduced pressure therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

In some embodiments, a negative pressure wound therapy apparatus includes a dressing configured to be placed over a wound and a source of negative pressure configured to be in fluid communication with the dressing. The source of negative pressure is configured to provide negative pressure to the wound. The apparatus can also include a canister configured to collect exudate removed from the wound. The canister can be configured to be in fluid communication with the dressing and the negative pressure source. The apparatus also includes a pressure sensor configured to monitor pressure signals generated by the negative pressure source and a controller. The controller can be configured to determine a level of exudate in the canister (or in the dressing) based at least in part on one or more characteristics of the monitored pressure signals. The one or more characteristics of the pressure signals can change as a level of exudate in the canister increases.

In various embodiments, a method of operating a negative pressure wound therapy apparatus includes monitoring pressure signals generated by a negative pressure source in fluid communication with a dressing and a canister. The method also includes determining a level of exudate in the canister (or in the dressing) based at least in part on one or more characteristics of the monitored pressure signals. The one or more characteristics of the pressure signals can change as a level of exudate in the canister increases.

In some embodiments, systems and methods for determining an amount of flow restriction or reduced volume in front of a negative pressure utilize one or more characteristics of monitored pressure signals. For example, the magnitude or frequency of the pressure signals can increase as restriction to flow increase, which effectively reduces the volume in front of a negative pressure source. The volume in front of the negative pressure source may decrease due to filling of a canister or dressing with exudate removed from a wound.

Negative Pressure System

FIG. 1 illustrates an embodiment of a negative or reduced pressure wound therapy (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity at atmospheric pressure, and also may have a substantially reduced compressed volume when under negative pressure. The wound cover 120 can provide a substantially fluid impermeable seal over the wound cavity 110. In some embodiments, the wound cover 120 has a top side and a bottom side, and the bottom side adhesively (or in any other suitable manner) seals with wound cavity 110. The conduit 140 or any other conduit disclosed herein can be formed from polyurethane, PVC, nylon, polyethylene, silicone, or any other suitable material.

Some embodiments of the wound cover 120 can have a port (not shown) configured to receive an end of the conduit 140. In some embodiments, the conduit 140 can otherwise pass through and/or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. In some embodiments, though not required, the pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

In some embodiments, the pump assembly 150 can be configured to deliver negative pressure at a desired negative pressure setpoint, which can be selected or programmed to be approximately −80 mmHg, or between about −20 mmHg and −200 mmHg (e.g., as selected by a user). Note that these pressures are relative to normal ambient atmospheric pressure thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively a pressure range of over approximately −100 mmHg, or even 150 mmHg, can be supplied by the pump assembly 150.

In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure set points. Low set point can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high set points and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2012/0116334, 2011/0213287, 2011/0282309, 2012/0136325, 2013/0110058, which are incorporated by reference in their entireties. In other embodiments, other suitable wound dressings can be utilized.

Reduced Pressure Therapy Systems and Methods

Figure 2:
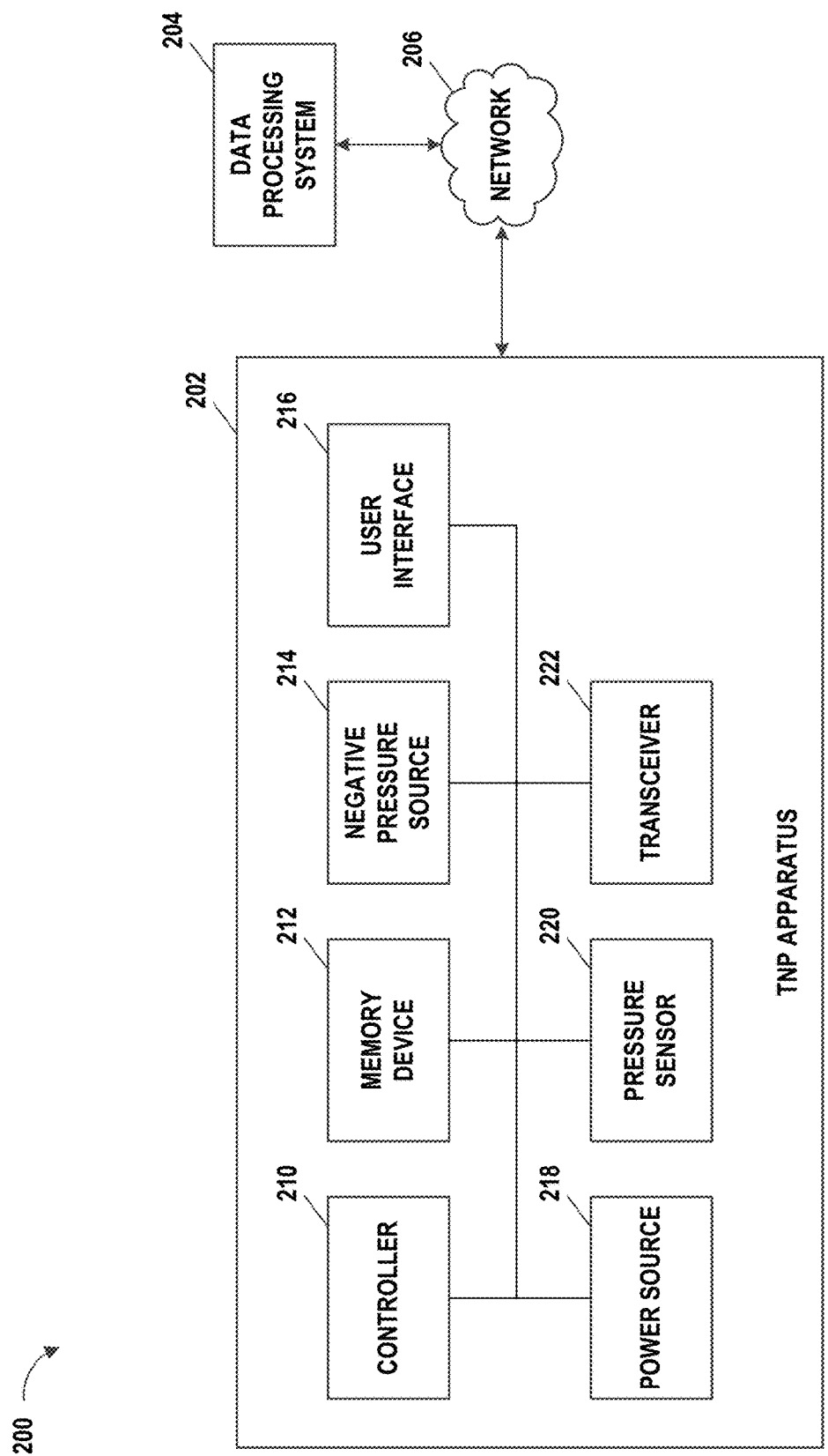
FIG. 2 illustrates a negative pressure therapy system that includes a TNP apparatus and a remote data processing system according to some embodiments.

FIG. 2 illustrates a negative pressure therapy system 200 that includes a TNP apparatus 202 and a remote data processing system 204. The TNP apparatus 202 can be used to treat a wound using a wound dressing that is in fluidic communication with the TNP apparatus 202 via a fluid flow path. The TNP apparatus 202 can include a controller 210, a memory device 212, a negative pressure source 214, a user interface 216, a power source 218, a pressure sensor 220, and a transceiver 222 that are configured to electrically communicate with one another. The power source 218 can provide power to one or more components of the TNP apparatus 202. The TNP apparatus 202 can operate at the pressure levels and at least partly in ways similar to those described in the '527 Application, or International App. No. PCT/US2014/050233 (hereinafter "the '233 Application"), published as WO 2015/023515, entitled Systems and Methods for Applying Reduced Pressure Therapy, each of which is incorporated by reference herein in its entirety. In addition, apparatus 202 can operate at the pressure levels that may differ from the '527 Application and/or the '233 Application, at least in some instances, as described herein.

The controller 210 can control operations of one or more other components of the TNP apparatus 202 according at least to instructions stored in the memory device 212. The controller 210 can, for instance, control operations of and supply of negative pressure by the negative pressure source 214. The negative pressure source 214 can include a pump, such as, without limitation, a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, or any other suitable pump or micropump or any combinations of the foregoing. The user interface 216 can include one or more elements that receive user inputs or provide user outputs to a patient or caregiver. The one or more elements that receive user inputs can include buttons, switches, dials, touch screens, or the like.

Figure 3:
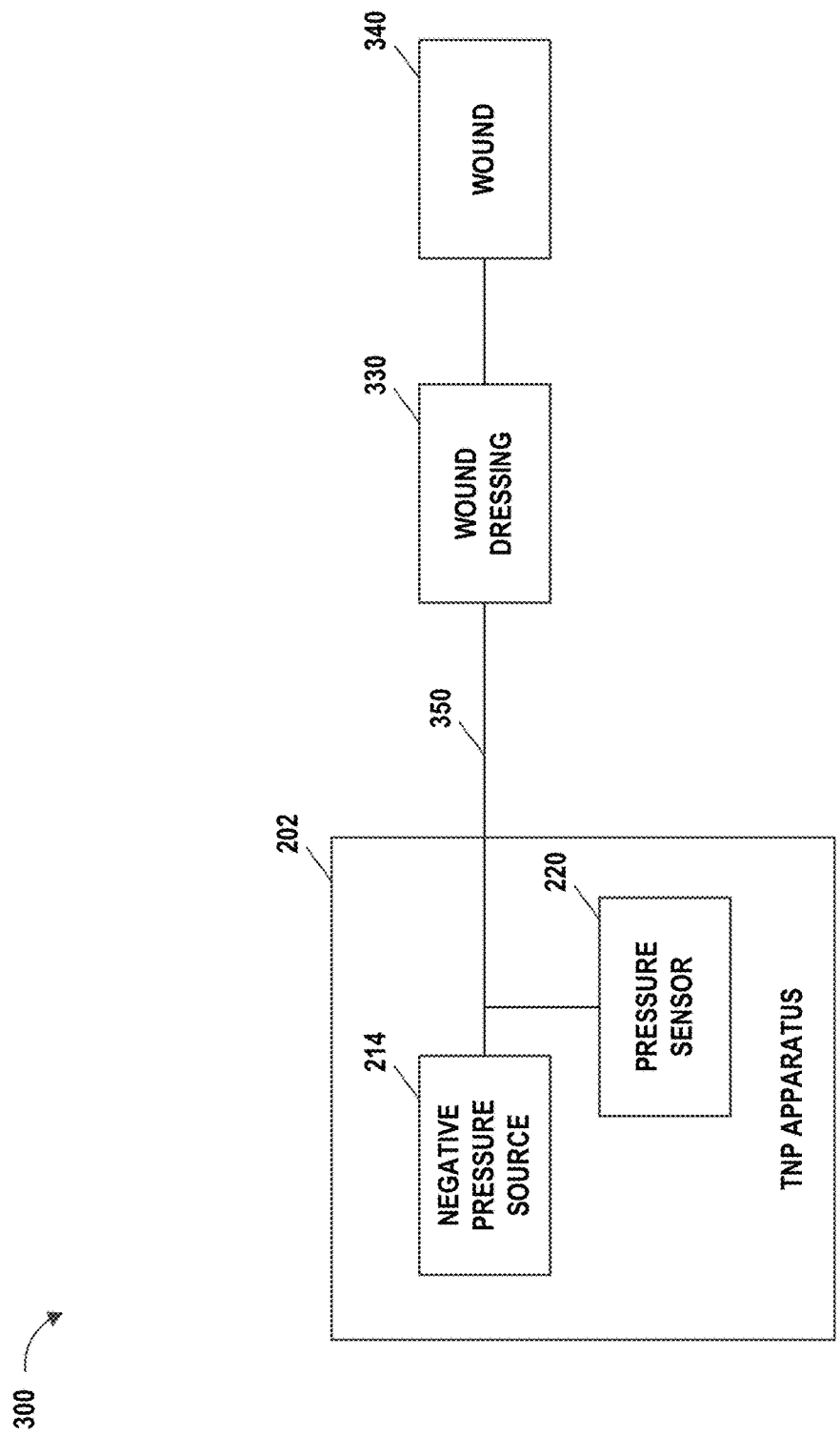
FIG. 3 illustrates an example of a negative pressure therapy system that includes the TNP apparatus of FIG. 2, as well as a first fluid flow path, a wound dressing, and a wound.
Figure 4:
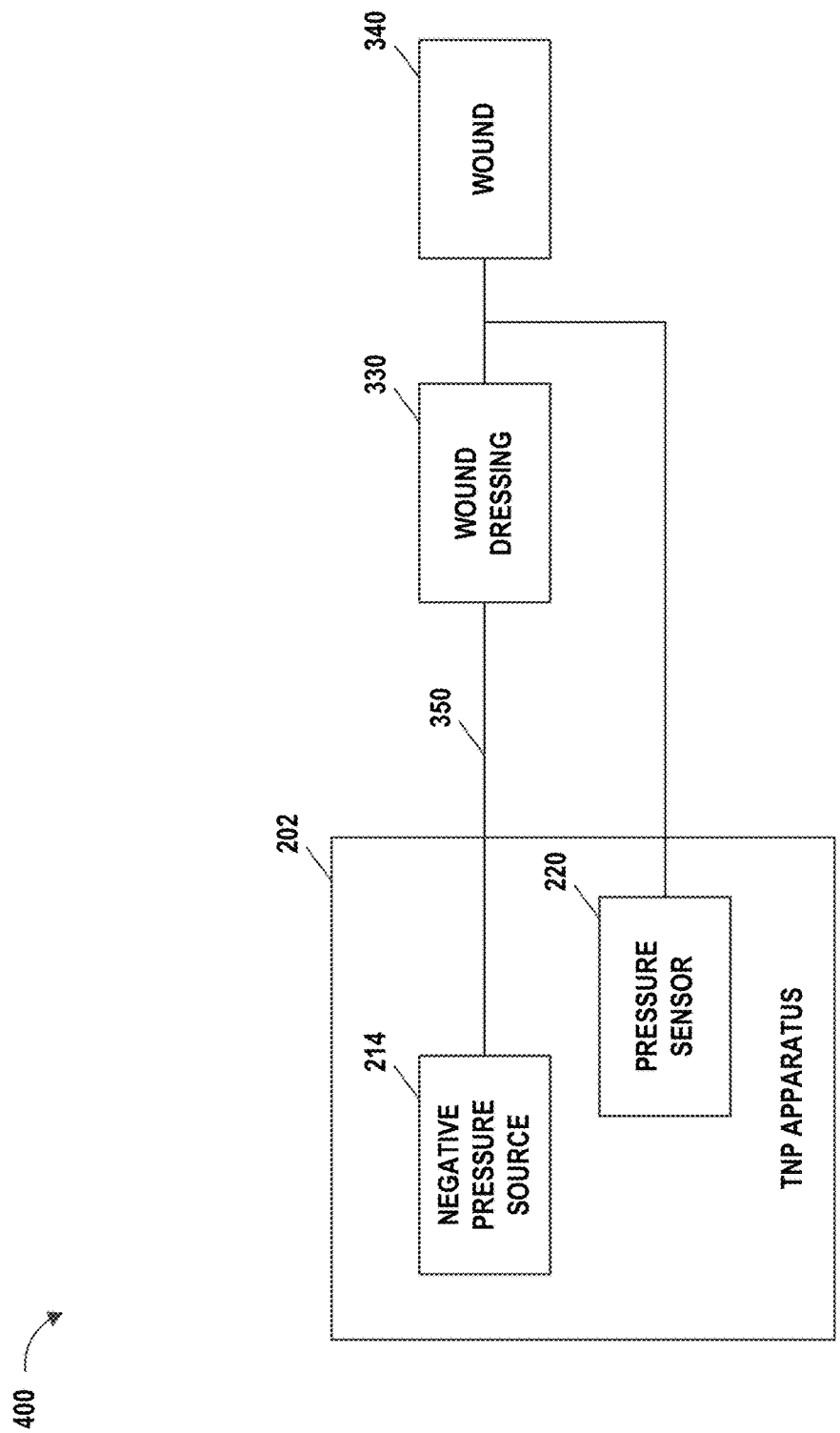
FIG. 4 illustrates a negative pressure therapy system that includes a pressure sensor positioned to measure pressure at or near a wound dressing according to some embodiments.
Figure 5:
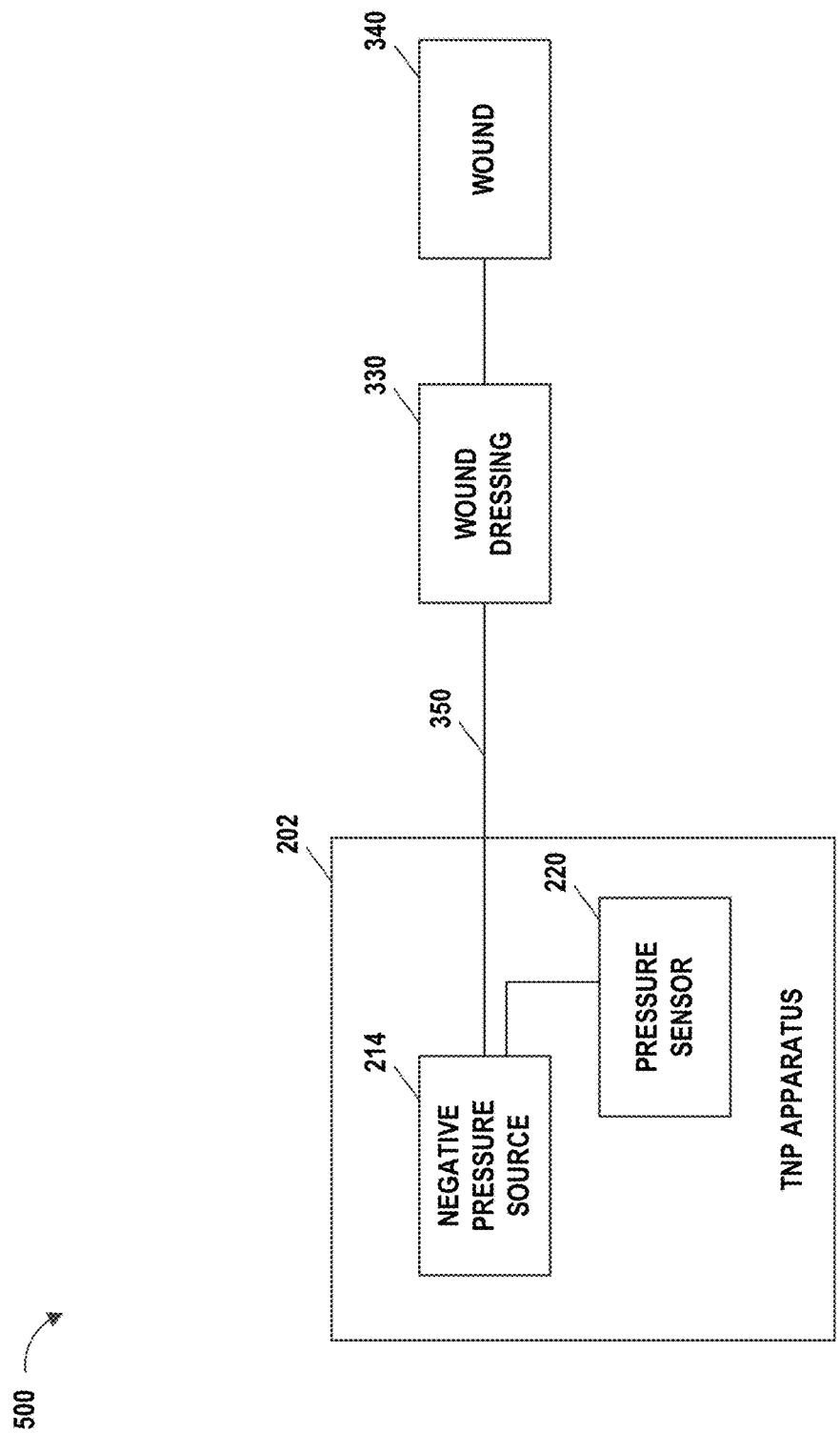
FIG. 5 illustrates a negative pressure therapy system that includes a pressure sensor positioned to measure pressure at the negative pressure source according to some embodiments.
Figure 8:
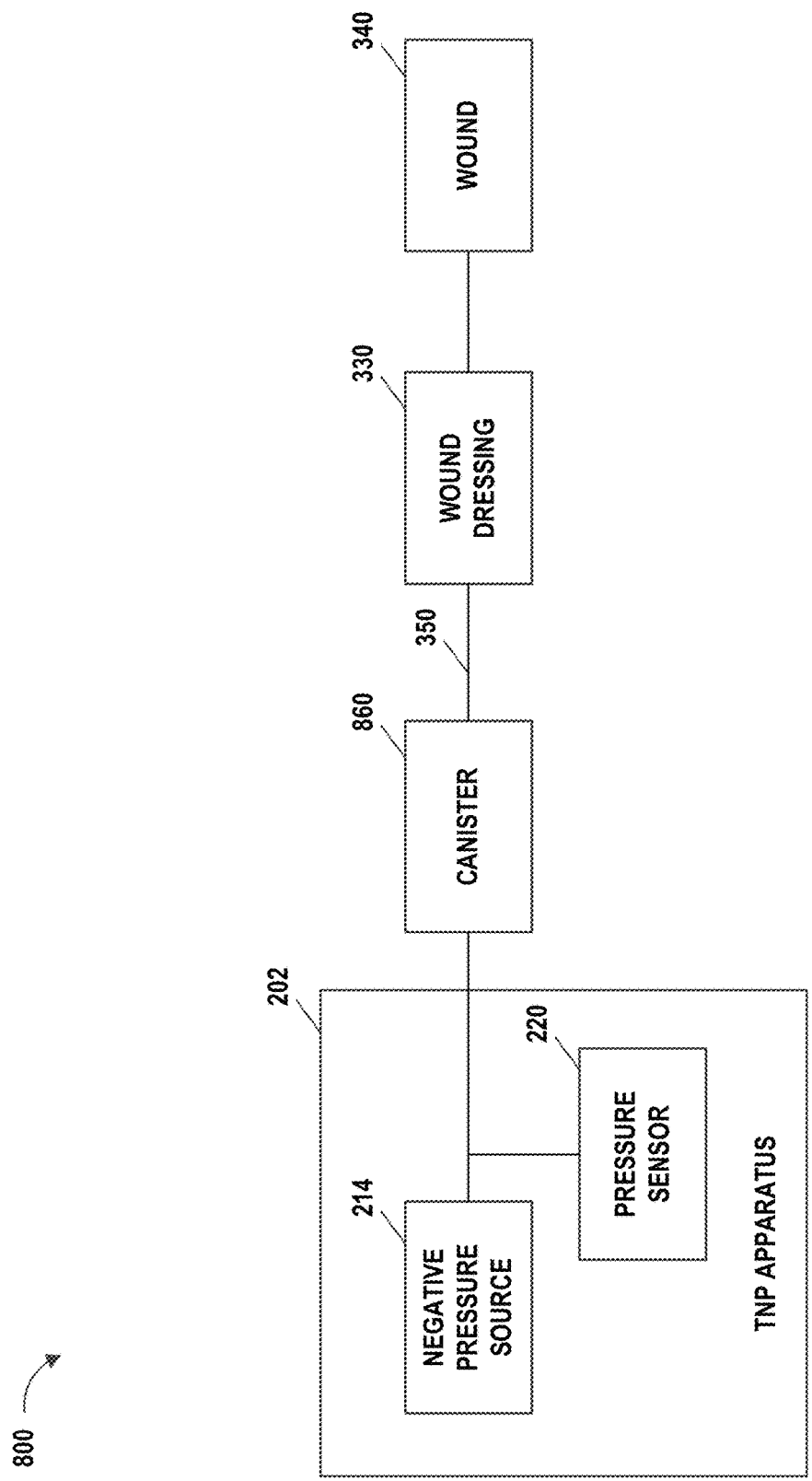
FIG. 8 illustrates a negative pressure therapy system that includes a canister coupled between the negative pressure source and the wound dressing in the first fluid flow path according to some embodiments.

The pressure sensor 220 can be used to monitor pressure underneath a wound dressing, such as (i) pressure in a fluid flow path 350 connecting the negative pressure source 214 and the wound dressing 330 as illustrated by FIG. 3, (ii) pressure at the wound dressing as illustrated by FIG. 4, or (iii) pressure at or in the negative pressure source 214 as illustrated by FIG. 5. In some implementations, the pressure sensor 220 can include at least two pressure sensors that are positioned in or fluidically connected to the fluid flow path to permit differential measurement of the pressure, such as illustrated by FIG. 8. For example, a first pressure sensor can be positioned upstream of the wound (such as at or near the inlet of the negative pressure source 214) and a second pressure sensor can be positioned to detect pressure at or near the wound or at or near a canister. This configuration can be accomplished by incorporating, in addition to one or more lumens forming a first fluid flow path connecting the negative pressure source 214 to the wound, a second fluid flow path that includes one or more lumens connecting the TNP apparatus 202 to the wound and through which the second pressure sensor can monitor pressure at or near the wound or at or near a canister. The first and second fluid flow paths can be fluidically isolated from each other. When the at least two pressure sensors are used, the rate of change of pressure (for example, in peak-to-peak pressure or maximum pressure) in the first and second fluid flow paths can be determined and the difference in pressure detected between the first and second pressure sensors can be determined. These values can be used separately or together to detect various operational conditions, such as leaks, blockages, canister full, presence of blood in the first fluid flow path or the second fluid flow path, etc. In some implementations, multiple redundant pressure sensors can be provided to protect against failure of one or more of the pressure sensors.

The transceiver 222 can be used to communicate with the data processing system 204 via a network 206. The transceiver 222 can, for example, transmit device usage data like alarms, measured pressure, or changes to a therapy program administered by the TNP apparatus 202 to the data processing system 204. The network 206 can be a communication network, such as a wireless communications network like a cellular communications network. The memory device 212 can be used to store the device usage data that may be transmitted by the transceiver 222. The data processing system 204 can, in some implementations, analyze pressure data received from the transceiver 222 to determine whether the received pressure data is indicative of patient compliance with a prescribed exercise regimen, such as using analysis approaches as described with respect to the TNP apparatus 202.

FIG. 3 illustrates a negative pressure therapy system 300 that includes the TNP apparatus 202 of FIG. 2, as well as a first fluid flow path 350, a wound dressing 330, and a wound 340. The TNP apparatus 202 can be used to treat the wound 340 using the wound dressing 330 that is in fluidic communication with the negative pressure source 214 via the first fluid flow path 350. In particular, FIG. 3 depicts that the pressure sensor 220 can be positioned in the first fluid flow path 350, such as at or near an inlet of the TNP apparatus 202, to measure pressure in the first fluid flow path 350.

FIG. 4 illustrates a negative pressure therapy system 400 that differs from the negative pressure therapy system 300 in that the pressure sensor 220 can instead be positioned to measure pressure at or near the wound dressing 330, such as pressure underneath the wound dressing 330 when the wound dressing 330 is coupled to the wound 340.

FIG. 5 illustrates a negative pressure therapy system 500 that differs from the negative pressure therapy system 300 in that the pressure sensor 220 can instead be positioned to measure pressure at the negative pressure source 214. In some examples, the pressure sensor 220 can be a part of and within the negative pressure source 214 to measure pressure generated by the negative pressure source 214. In another example, the pressure sensor 220 can be separate from the negative pressure source 214 and positioned to measure pressure at or near an inlet of the negative pressure source 214.

Figure 6:
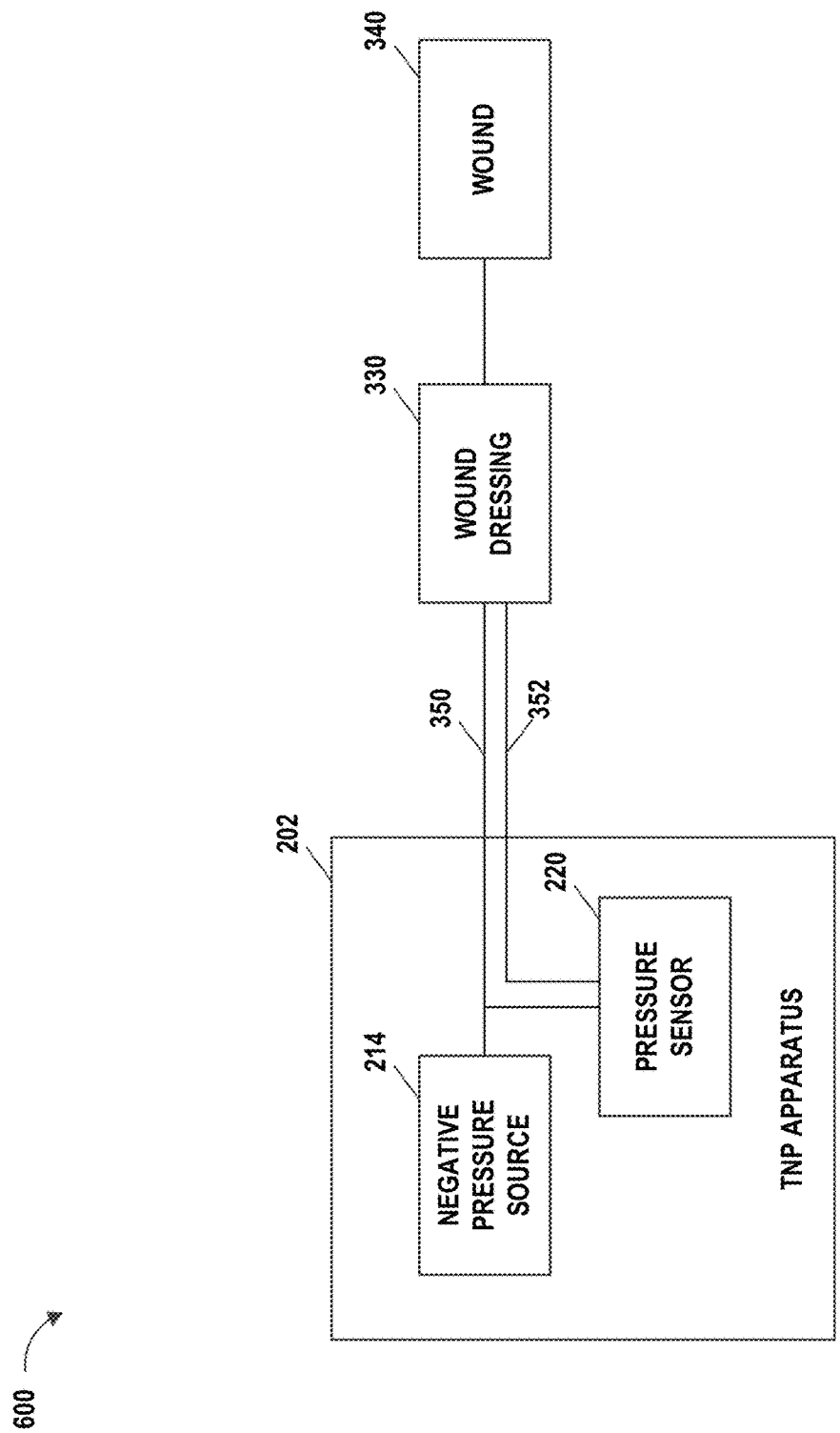
FIG. 6 illustrates a negative pressure therapy system that includes a second fluid flow path and a pressure sensor that can be a differential pressure sensor or include two pressure sensors according to some embodiments.

FIG. 6 illustrates a negative pressure therapy system 600 that differs from the negative pressure therapy system 300 in that the negative pressure therapy system 600 further includes a second fluid flow path 352, and the pressure sensor 220 can be a differential pressure sensor or include two pressure sensors. If the pressure sensor 220 includes the two pressure sensors, one of the two pressure sensors of the pressure sensor 220 can be positioned in the first fluid flow path 350 to measure pressure in the first fluid flow path 350, and the other of the two pressure sensors the pressure sensor 220 can be positioned in the second fluid flow path 352 to measure pressure in the second fluid flow path 352. If the pressure sensor 220 is the differential pressure sensor, the pressure sensor 220 can be fluidically connected to the first fluid flow path 350 and the second fluid flow path 352. The first fluid flow path 350 can thus be used by the negative pressure source 214 to provide negative pressure to the wound dressing 330, and the second fluid flow path 352 can be used primarily by the pressure sensor 220 to measure pressure at or near the wound dressing 330, such as under the wound dressing 330. The pressure sensor 220 can thereby be used by the TNP apparatus 202 to perform differential measurement of pressure between pressure supplied by the negative pressure source 214 and pressure at or near the wound dressing 330.

Figure 7:
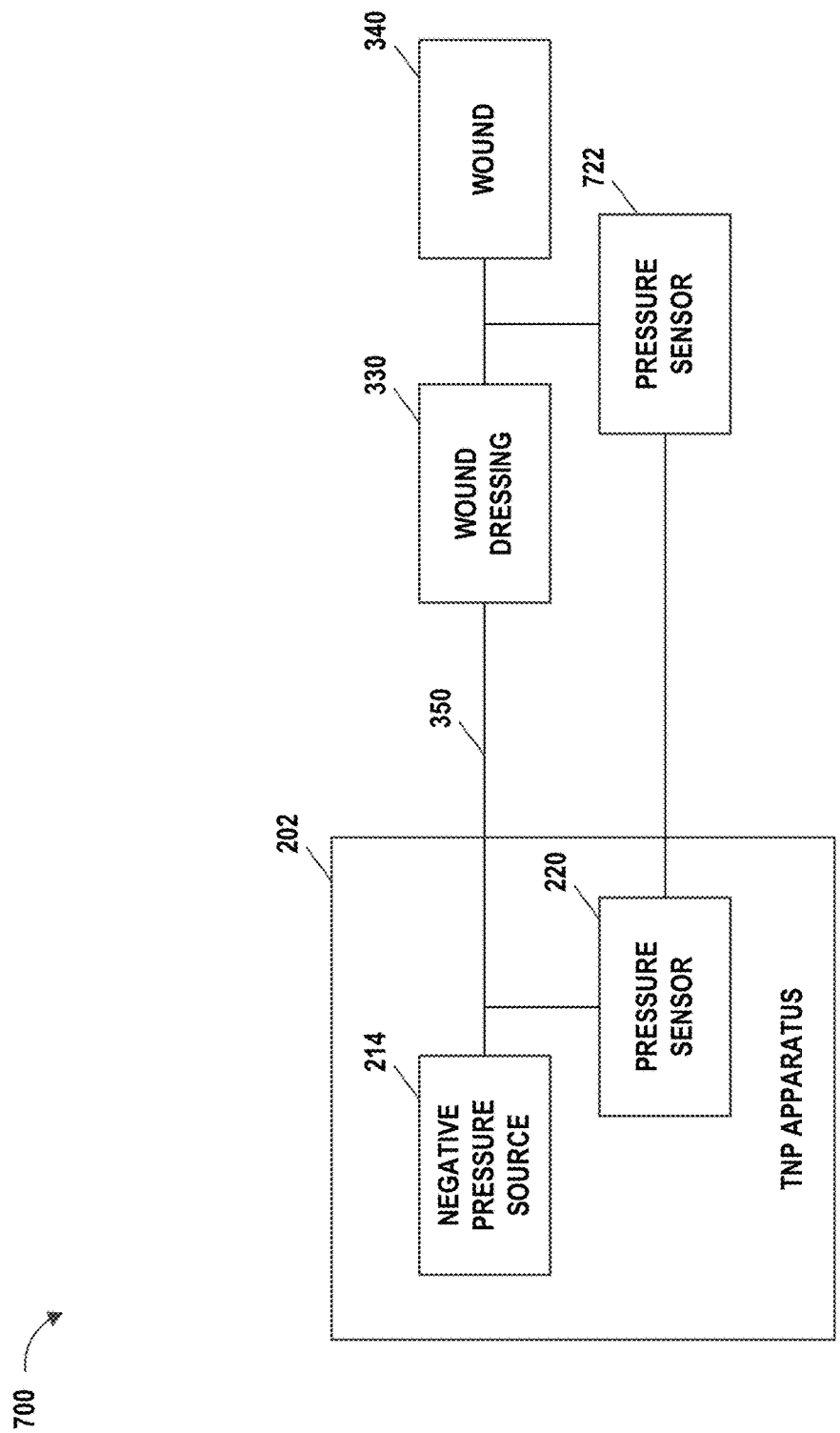
FIG. 7 illustrates a negative pressure therapy system that includes an additional pressure sensor positioned to measure pressure at or near a wound dressing according to some embodiments.

FIG. 7 illustrates a negative pressure therapy system 700 that differs from the negative pressure therapy system 300 in that the negative pressure therapy system 700 can further include an additional pressure sensor 722 positioned to measure pressure at or near the wound dressing 330, such as pressure underneath the wound dressing 330 when the wound dressing 330 is coupled to the wound 340. The additional pressure sensor 722 can generate and output a signal to the TNP apparatus 202 responsive to the pressure measured at the wound dressing 330. The pressure sensor 220 and the additional pressure sensor 722 can thus be used by the TNP apparatus 202 to perform differential measurement of pressure between pressure supplied by the negative pressure source 214 and pressure at or near the wound dressing 330. In any of the embodiments described herein, the pressure sensor 220 can be used alone or in combination with the additional pressure sensor 722.

FIG. 8 illustrates a negative pressure therapy system 800 that differs from the negative pressure therapy system 300 in that a canister 860 can be coupled between the negative pressure source 214 and the wound dressing 330 in the first fluid flow path 350. The canister 860 can collect exudate removed from the wound 340. The examples of FIGS. 2-7 can be similarly modified to also include the canister 860, in some implementations.

Figure 9:
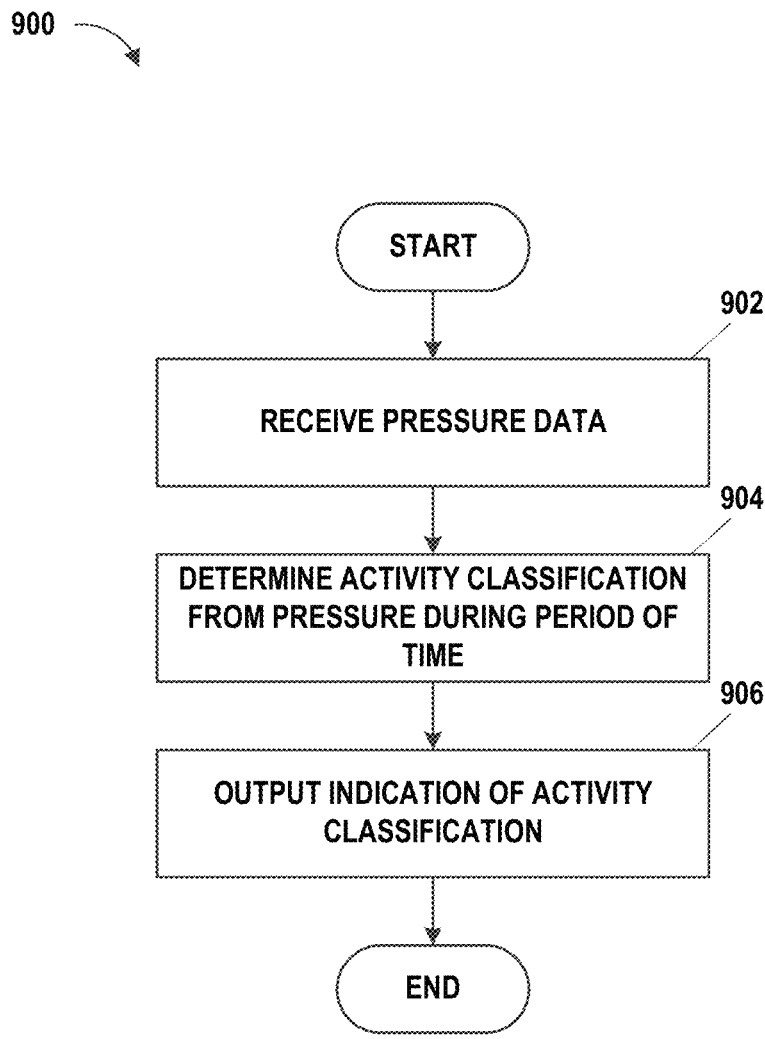
FIG. 9 illustrates a patient activity classification process according to some embodiments.

FIG. 9 illustrates a patient activity classification process 900 performable by a device, such as the TNP apparatus 202 of FIGS. 2-8, the negative pressure unit 150 of FIG. 1A of the '527 Application, the pump assembly 150 of FIG. 1 of the '233 Application, the pump assembly 230 of FIG. 2 of the '233 Application, or other pump assemblies described in the '527 Application or the '233 Application. In some embodiments, the process 900 can be implemented by the controller 210. For convenience, the patient activity classification process 900 is described in the context of the TNP apparatus 202 of FIGS. 2-8, but may instead be implemented in other systems described herein, in the '527 Application or the '233 Application, or by other computing systems not shown. The patient activity classification process 900 can advantageously, in certain embodiments, enable the TNP apparatus 202 to determine an activity classification for movement of a patient over a period of time and output an indication of the activity classification for presentation to a patient or clinician or to determine compliance with an exercise regimen by a patient.

At block 902, the process 900 can receive pressure data indicative of a magnitude or frequency of pressure measured in a fluid flow path coupling the negative pressure source 214 to a wound dressing. For example, the process 900 can receive pressure data indicative of an amplitude, magnitude, peak-to-peak, or peak-to-trough value of one or more pressure pulses. The wound dressing, such as one of the wound dressings described in the '527 Application, can be coupled to a patient, such as to the patient's knee, heel, elbow, shoulder, hip, torso or abdomen. The pressure can be measured, for instance, by the pressure sensor 220 using measurement approaches as described in the '233 Application. The pressure sensor 220 can communicate information via a wire or wirelessly to the process 900. In certain implementations, the pressure sensor 220 can be positioned at or near the wound and wirelessly communicate information to the process 900. In some embodiments, pressure sensor data includes one or more magnitudes of pressure measured over a duration of time, such as 0.5 seconds, 1 second, 3 seconds, and the like.

At block 904, the process 900 can determine an activity classification from pressure during a period of time using the pressure data. The process 900 can, for instance, analyze a change in a magnitude of the pressure over time during the time period (such as during the time period of at least 1 second, 10 seconds, 30 seconds, 1 minute, or 5 minutes). The activity classification can include, in some instances, one or more of sitting, walking, standing, breathing, jumping, traversing stairs, leg extending, leg bending, or performing chair squats by a patient wearing the wound dressing. In some example implementations, the process 900 can compare the magnitude of pressure over time to one or more pressure patterns or other measures of variation, such as one or more patterns or measures stored in the memory device 212, to determine the appropriate activity classification from the pressure during the time period.

At block 906, the process 900 can output an indication denoting the activity classification. The indication can be output, for example, by one or more of: outputting the indication for storage in the memory device 212, transmitting the indication to the data processing system 204 via the transceiver 222, outputting the indication for presentation to a user via the user interface 216, or storing the indication in association with device usage data of the TNP apparatus 202. The outputting of the indication can additionally control operations of the TNP apparatus 202, such as to enable or disable continued activation of the negative pressure source 214. In some examples, the outputting of the indication can allow the TNP apparatus 202 to detect when a patient is mobile, and the TNP apparatus can thus deactivate the negative pressure source 214 or cause the TNP apparatus 202 to enter a hibernation mode according to the indication.

Figure 10:
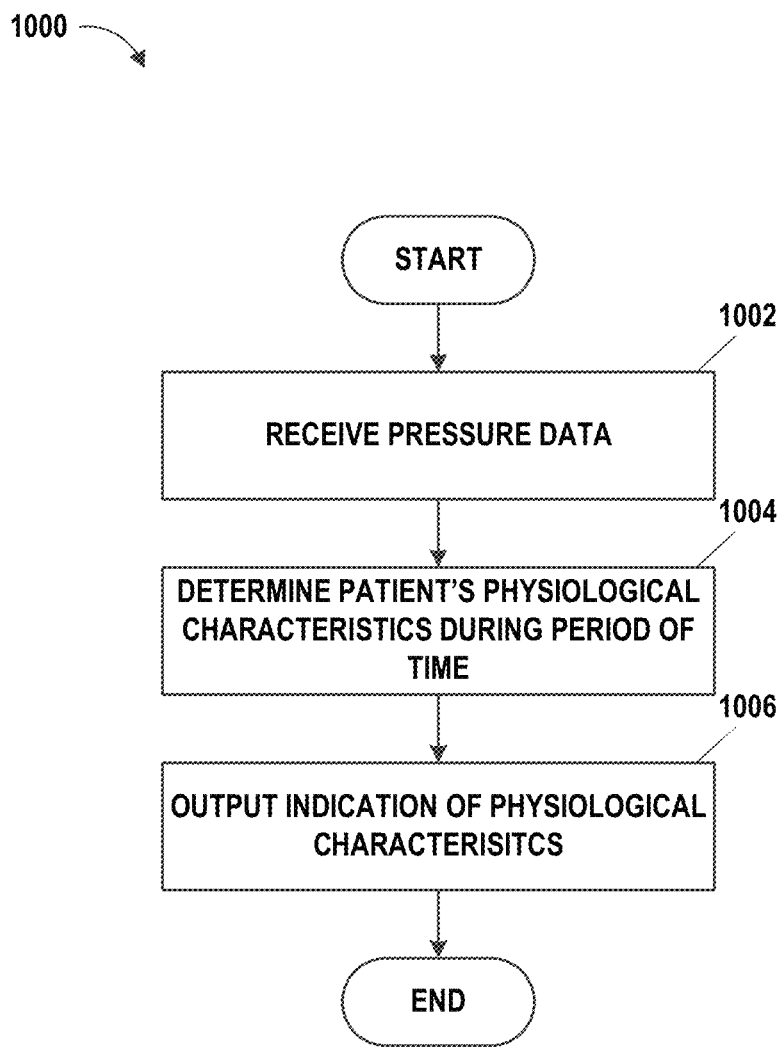
FIG. 10 illustrates a process for determining a patient's physiological characteristics according to some embodiments.

FIG. 10 illustrates a process 1000 for determining a patient's physiological characteristics performable by a device, such as the TNP apparatus 202 of FIGS. 2-8, the negative pressure unit 150 of FIG. 1A of the '527 Application, the pump assembly 150 of FIG. 1 of the '233 Application, the pump assembly 230 of FIG. 2 of the '233 Application, or other pump assemblies described in the '527 Application or the '233 Application. In some embodiments, the process 1000 can be implemented by the controller 210. For convenience, a process 1000 for determining a patient's physiological characteristics is described in the context of the TNP apparatus 202 of FIGS. 2-8, but may instead be implemented in other systems described herein, in the '527 Application or the '233 Application, or by other computing systems not shown. The patient activity classification process 1000 can advantageously, in certain embodiments, enable the TNP apparatus 202 to determine a patient's physiological characteristics over a period of time and output an indication of the physiological characteristics for presentation to a patient or clinician.

At block 1002, the process 1000 can receive pressure data indicative of a magnitude of pressure measured in a fluid flow path coupling the negative pressure source 214 to a wound dressing. The wound dressing, such as one of the wound dressings described in the '527 Application can be coupled to a patient, such as to the patient's knee, heel, elbow, shoulder, hip, torso or abdomen. The pressure can be measured, for instance, by the pressure sensor 220 using measurement approaches as described in the '233 Application. The pressure sensor 220 can communicate information via a wire or wirelessly to the process 1000. In certain implementations, the pressure sensor 220 can be positioned at or near the wound and wirelessly communicate information to the process 1000. In some embodiments, pressure sensor data includes one or more magnitudes of pressure measured over a duration of time, such as 0.5, 1, 2, 3, 6, 10, 30 or 60 seconds, and the like.

At block 1004, the process 1000 can determine physiological characteristics from pressure during a period of time using the pressure data. The process 1000 can, for instance, analyze a change in a magnitude of the pressure over time during the time period (such as during the time period of at least 1 second, 10 seconds, 30 seconds, 1 minute, or 5 minutes). The physiological characteristics can include, in some instances, one or more of respiration rate, pulse, or heart rate of a patient wearing the wound dressing. In some example implementations, the process 1000 can compare the magnitude of pressure over time to one or more pressure patterns or other measures of variation, such as one or more patterns or measures stored in the memory device 212, to determine the appropriate a change in physiological characteristics of the patient during the time period as compared to the patients average physiological characteristics.

At block 1006, the process 1000 can output an indication denoting the physiological characteristics. The indication can be output, for example, by one or more of: outputting the indication for storage in the memory device 212, transmitting the indication to the data processing system 204 via the transceiver 222, outputting the indication for presentation to a user via the user interface 216, or storing the indication in association with device usage data of the TNP apparatus 202. The outputting of the indication can additionally control operations of the TNP apparatus 202, such as to enable or disable continued activation of the negative pressure source 214. In some examples, the outputting of the indication can allow the TNP apparatus 202 to detect when a patient has abnormal physiological characteristics, and the TNP apparatus can thus deactivate the negative pressure source 214, send an alarm to the patient or a caregiver, increase a sampling rate of pressure data, and the like.

Figure 11:
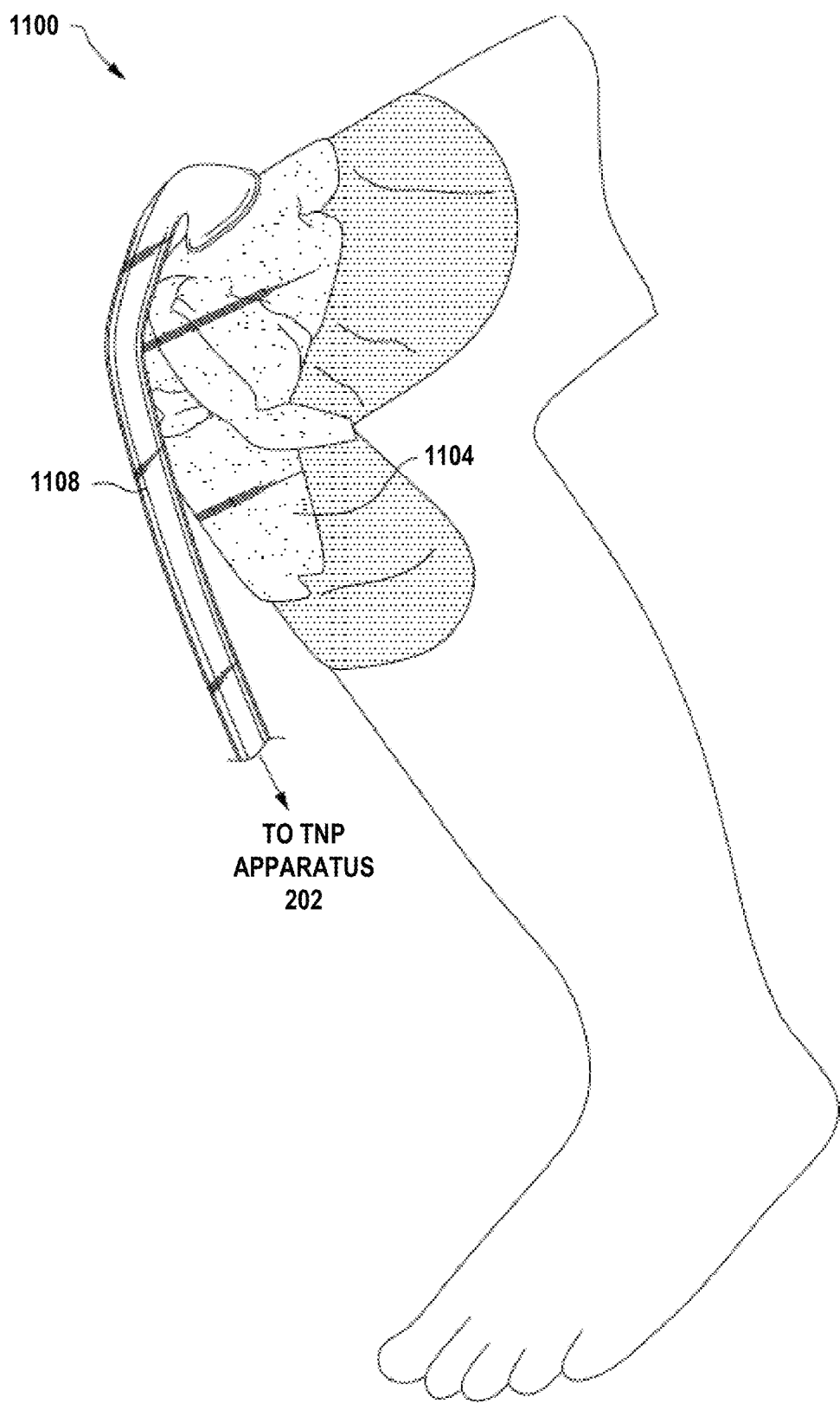
FIG. 11 illustrates a negative pressure wound therapy system in which a wound dressing is attached to a patient's knee and coupled to a TNP apparatus via a fluid flow path.

FIG. 11 illustrates an example of a TNP system 1100 in which a wound dressing 1104, which can be one implementation of the wound dressing 330, is attached to a patient's knee and coupled to the TNP apparatus 202 via a fluid flow path 1108, which can be one implementation of the first fluid flow path 350. The TNP apparatus 202 can provide negative pressure wound therapy to the patient's knee via the fluid flow path 1108 and the wound dressing 1104, as well as monitor, track, and report movement by the patient while the TNP apparatus 202 maintains negative pressure under the wound dressing below a negative pressure threshold. The TNP apparatus 202 can be performing negative pressure therapy when negative pressure under the wound dressing is maintained below the negative pressure threshold.

FIGS. 12-17 illustrate example pressure variations over time in the TNP system 1100 of FIG. 11 while the TNP apparatus 202 maintains negative pressure under the wound dressing below a negative pressure threshold. The pressure in the TNP system can, for instance, vary by around 5 mmHg to 20 mmHg due to movement of the patient as illustrated.

Figure 12:
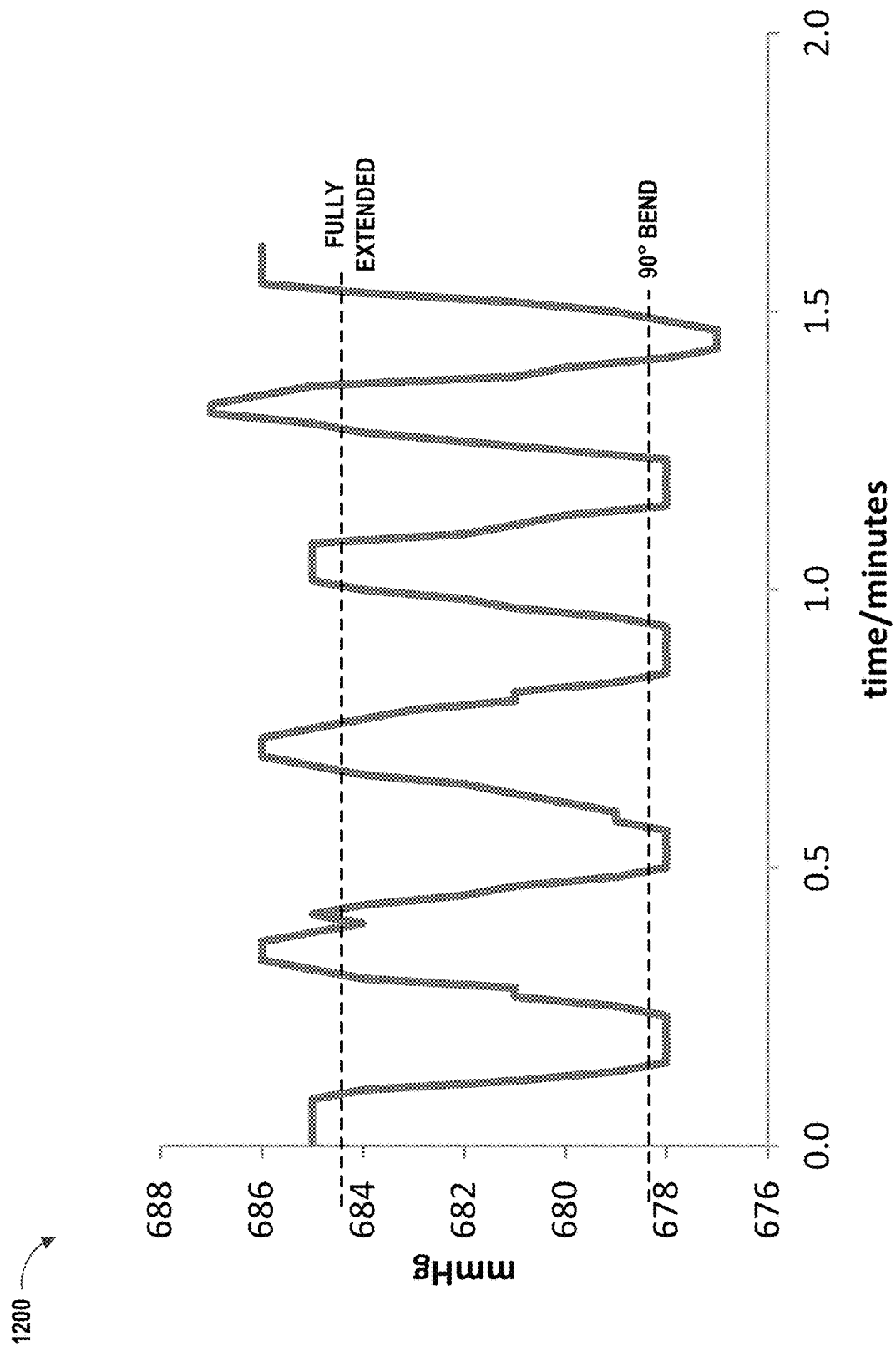
FIG. 12 provides a plot which illustrates how a magnitude of pressure measured by a pressure sensor can be used to determine an activity classification for a patient according to some embodiments.
Figure 13:
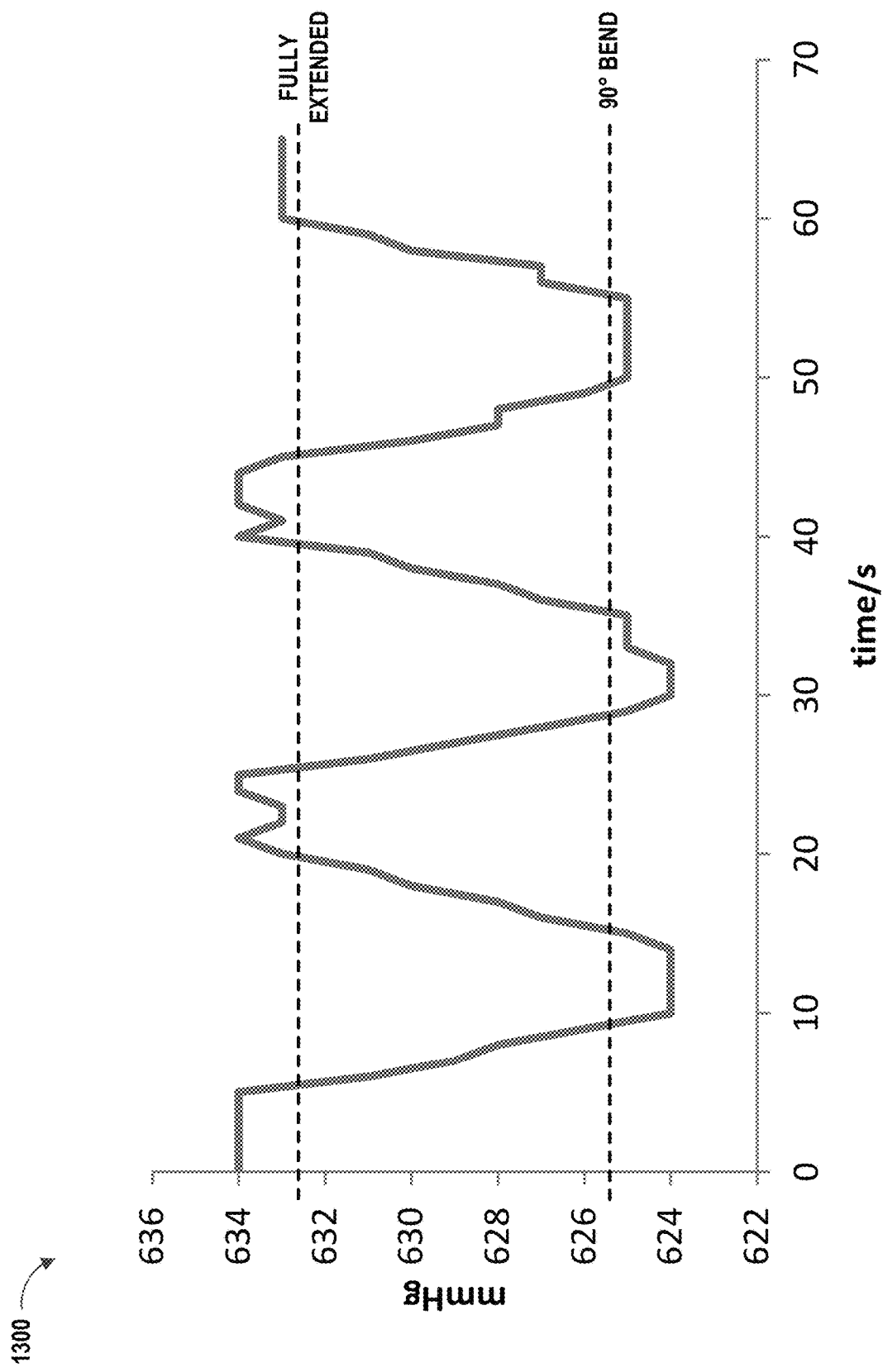
FIG. 13 provides a plot which illustrates how a magnitude of pressure measured by a pressure sensor can be used to determine an activity classification for a patient according to some embodiments.

FIGS. 12 and 13 provide a plot 1200 and a plot 1300 which illustrate how a magnitude of pressure measured by the pressure sensor 220 can be used to determine an activity classification for a patient. In response to the magnitude of pressure rising above a fully extended threshold shown in the plot 1200 or remaining above the fully extended threshold shown in the plot 1200 for a period of time (for example, 1, 2, 3, 5, 7, 10, or 20 seconds), a controller, such as the controller 210, can determine that the patient is fully extending the knee. In response to the magnitude of pressure falling below a 90° bend threshold shown in the plot 1200 or remaining below the 90° bend threshold shown in the plot 1200 for a period of time (for example, 1, 2, 3, 5, 7, 10, or 20 seconds), the controller 210 can determine that the patient is bending the knee at the angle of 90°. In response to the magnitude of pressure rising above a fully extended threshold shown in the plot 1300 or remaining above the fully extended threshold shown in the plot 1300 for a period of time (for example, 1, 2, 3, 5, 7, 10, or 20 seconds), the controller 210 can determine that the patient is fully extending the knee. In response to the magnitude of pressure falling below a 90° bend threshold shown in the plot 1300 or remaining below the 90° bend threshold shown in the plot 1300 for a period of time (for example, 1, 2, 3, 5, 7, 10, or 20 seconds), the controller 210 can determine that the patient is bending the knee at the angle of 90°.

Figure 14:
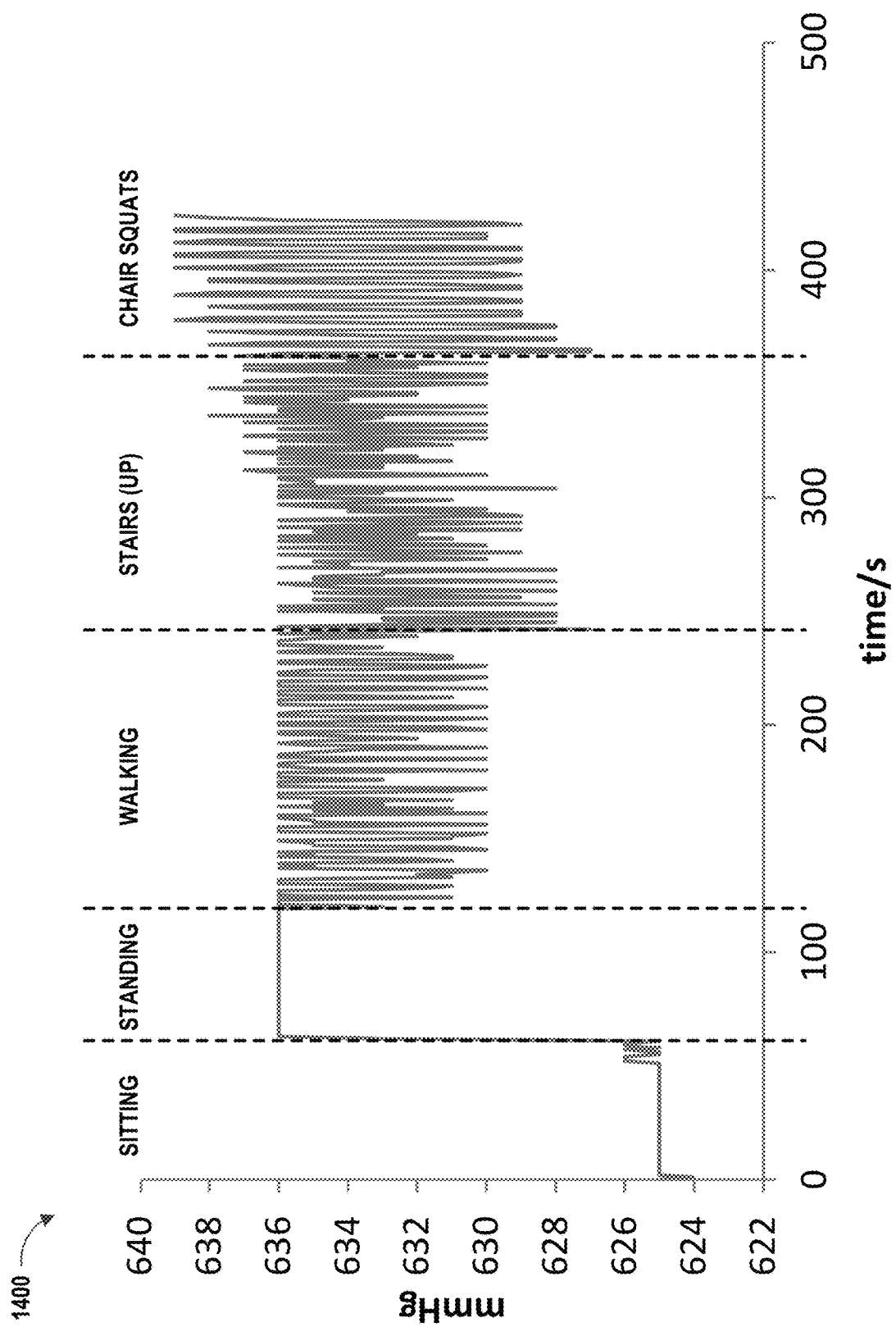
FIG. 14 provides a plot which illustrates how a magnitude or frequency of pressure measured by a pressure sensor can be used to determine an activity classification for a patient according to some embodiments.

FIG. 14 provides a plot 1400 which illustrates how a magnitude or frequency of pressure measured by the pressure sensor 220 can be used to determine an activity classification for a patient.

A controller, such as the controller 210, can determine that the patient is sitting in various ways. For example, if the magnitude of pressure is at around a sitting threshold (e.g., about 625 mmHg), remains at around the sitting threshold for a period of time (for example, 1, 2, 3, 5, 7, 10, or 20 seconds), or varies a relatively minimal amount over time (as illustrated by a sitting period illustrated in the plot 1400), the controller 210 can determine that the patient is sitting. Similarly, the controller can determine that the patient is sitting based on peak-to-peak pressure values. For example, if the peak-to-peak value of the pressure pulses is approximately zero, the controller can determine that the patient is not moving (e.g., is sitting).

Furthermore, in some embodiments, frequency of the pressure signal can be used in addition to or instead of changes in amplitude for determination of an activity classification. For example, as is shown in FIG. 14, the frequency of the detected pressure signal decreases or drops as the patient moves less or becomes more still. The frequency of the detected pressure signal can be compared to one or more frequency thresholds, which may be determined to detect that the patient is sitting.

The controller 210 can determine that the patient is standing in various ways. For example, if the magnitude of pressure is at around a standing threshold (e.g., 636 mmHg), remains at around the standing threshold for a period of time (for example, 1, 2, 3, 5, 7, 10, or 20 seconds), or varies a relatively minimal amount over time as illustrated by a standing period illustrated in the plot 1400, the controller 210 can determine that the patient is standing. Similarly, the controller can determine that the patient is standing based on peak-to-peak pressure values. For example, if the peak-to-peak value of the pressure pulses is approximately zero, the controller can determine that the patient is not moving (e.g., is standing).

Furthermore, in some embodiments, frequency of the pressure signal can be used in addition to or instead of changes in amplitude for determination of an activity classification. For example, as is shown in FIG. 14, the frequency of the detected pressure signal decreases or drops as the patient moves less or becomes more still. The frequency of the detected pressure signal can be compared to one or more frequency thresholds, which may be determined to detect that the patient is standing.

The controller 210 can determine that the patient is walking in various ways. For example, if the magnitude of pressure is at around the standing threshold, remains at around the sitting threshold for a period of time (for example, 1, 2, 3, 5, 7, 10, or 20 seconds), or varies a relatively moderate amount over time as illustrated by a walking period illustrated in the plot 1400, the controller 210 can determine that the patient is walking. Similarly, the controller can determine that the patient is walking based on peak-to-peak pressure values. If the peak-to-peak value of the pressure pulses is approximately equal to the standing threshold minus a relatively moderate amount (e.g. 1, 2, 3, 4, 5, 6, 7, 8, 9, or 10 mmHg), the controller can determine that the patient is moving (e.g., walking). For example, if the peak-to-peak pressure value is approximately 4, 5, 6, 7, or 8 mmHg, the controller may determine that the patient is walking.

Furthermore, in some embodiments, frequency of the pressure signal can be used in addition to or instead of changes in amplitude for determination of an activity classification. For example, as is shown in FIG. 14, the frequency of the detected pressure signal increases as the patient moves or becomes more active. The frequency of the detected pressure signal can be compared to one or more frequency thresholds, which may be determined to detect that the patient is walking.

The controller 210 can determine that the patient is moving up a set of stairs in various ways. For example, if the magnitude of pressure is at around the standing threshold, remains at around the sitting threshold for a period of time (for example, 1, 2, 3, 5, 7, 10, or 20 seconds), or varies a relatively significant amount over time as illustrated by a stair (up) period illustrated in the plot 1400, the controller 210 can determine that the patient is walking up stairs. Similarly, the controller can determine that the patient is walking up a set of stairs based on peak-to-peak pressure values. If the peak-to-peak value of the pressure pulses is more than the peak-to-peak values associated with walking by a relatively moderate amount (e.g. 1, 2, 3, 4, 5, 6, 7, 8, 9, or 10 mmHg), the controller can determine that the patient is moving (e.g., walking up a set of stairs). For example, if the peak-to-peak pressure value is approximately 6, 7, 8, 9, or 10 mmHg, the controller may determine that the patient is walking up a set of stairs.

Furthermore, in some embodiments, frequency of the pressure signal can be used in addition to or instead of changes in amplitude for determination of an activity classification. For example, as is shown in FIG. 14, the frequency of the detected pressure signal increases as the patient moves or becomes more active. The frequency of the detected pressure signal can be compared to one or more frequency thresholds, which may be determined to detect that the patient is walking up stairs.

The controller 210 can determine that the patient is doing chair squats in various ways. For example, if the magnitude of pressure is at around the standing threshold, remains at around the sitting threshold for a period of time (for example, 1, 2, 3, 5, 7, 10, or 20 seconds), or varies a relatively significant amount over time as illustrated by a chair squats period illustrated in the plot 1400, the controller 210 can determine that the patient is performing chair squats. Similarly, the controller can determine that the patient is doing chair squats based on peak-to-peak pressure values. If the peak-to-peak value of the pressure pulses is more than the peak-to-peak values associated with walking and/or walking up a set of stairs by a relatively moderate amount (e.g. 1, 2, 3, 4, 5, 6, 7, 8, 9, or 10 mmHg), the controller can determine that the patient is moving (e.g., doing chair squats). For example, if the peak-to-peak pressure value is approximately 8, 9, 10, 11, or 12 mmHg, the controller may determine that the patient is doing chair squats.

Furthermore, in some embodiments, frequency of the pressure signal can be used in addition to or instead of changes in amplitude for determination of an activity classification. For example, as is shown in FIG. 14, the frequency of the detected pressure signal increases as the patient moves or becomes more active. The frequency of the detected pressure signal can be compared to one or more frequency thresholds, which may be determined to detect that the patient is doing chair squats.

Figure 15:
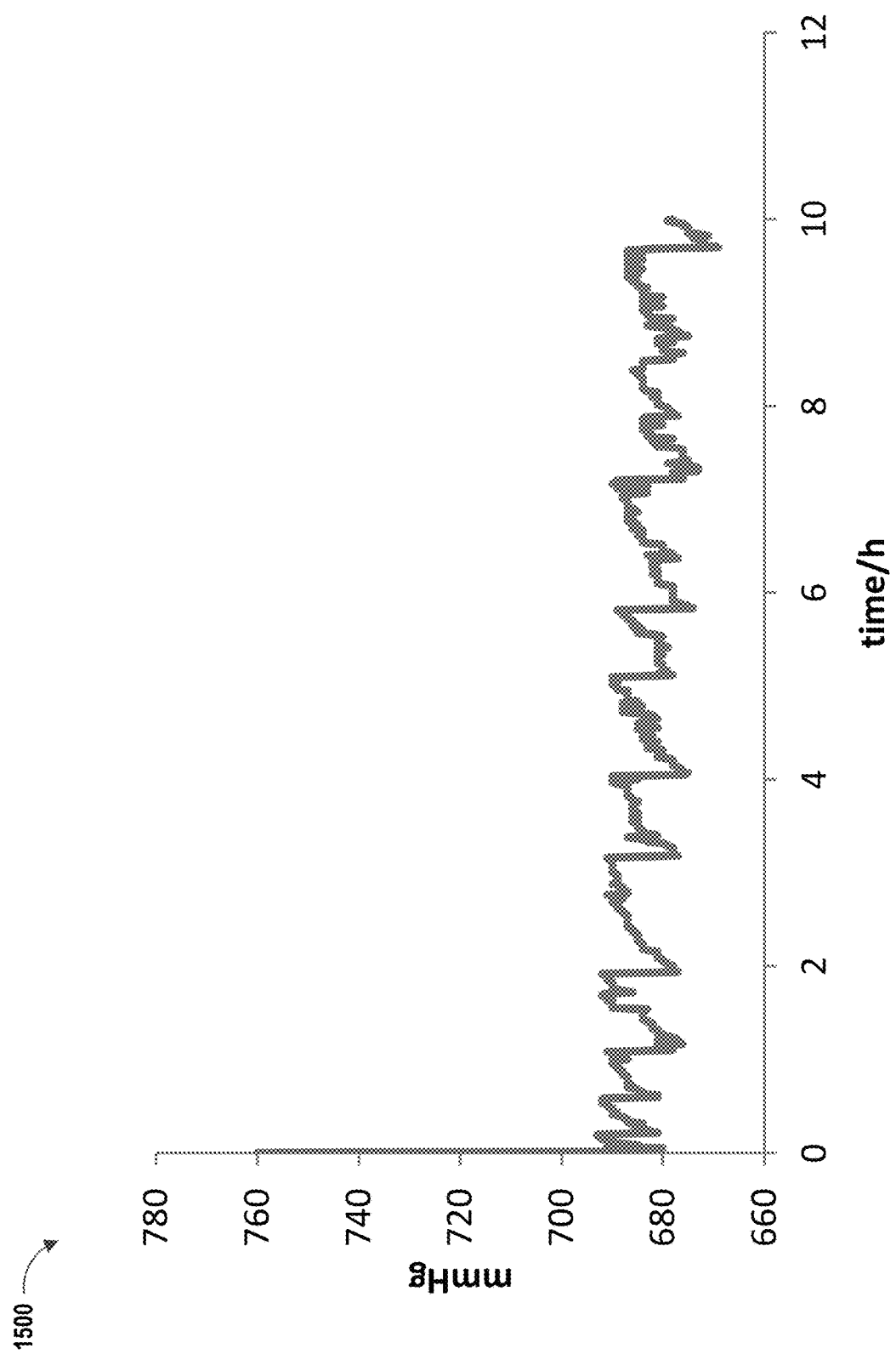
FIG. 15 provides a plot which illustrates how a magnitude of pressure measured by the pressure sensor can change over different wears by a patient according to some embodiments.
Figure 16:
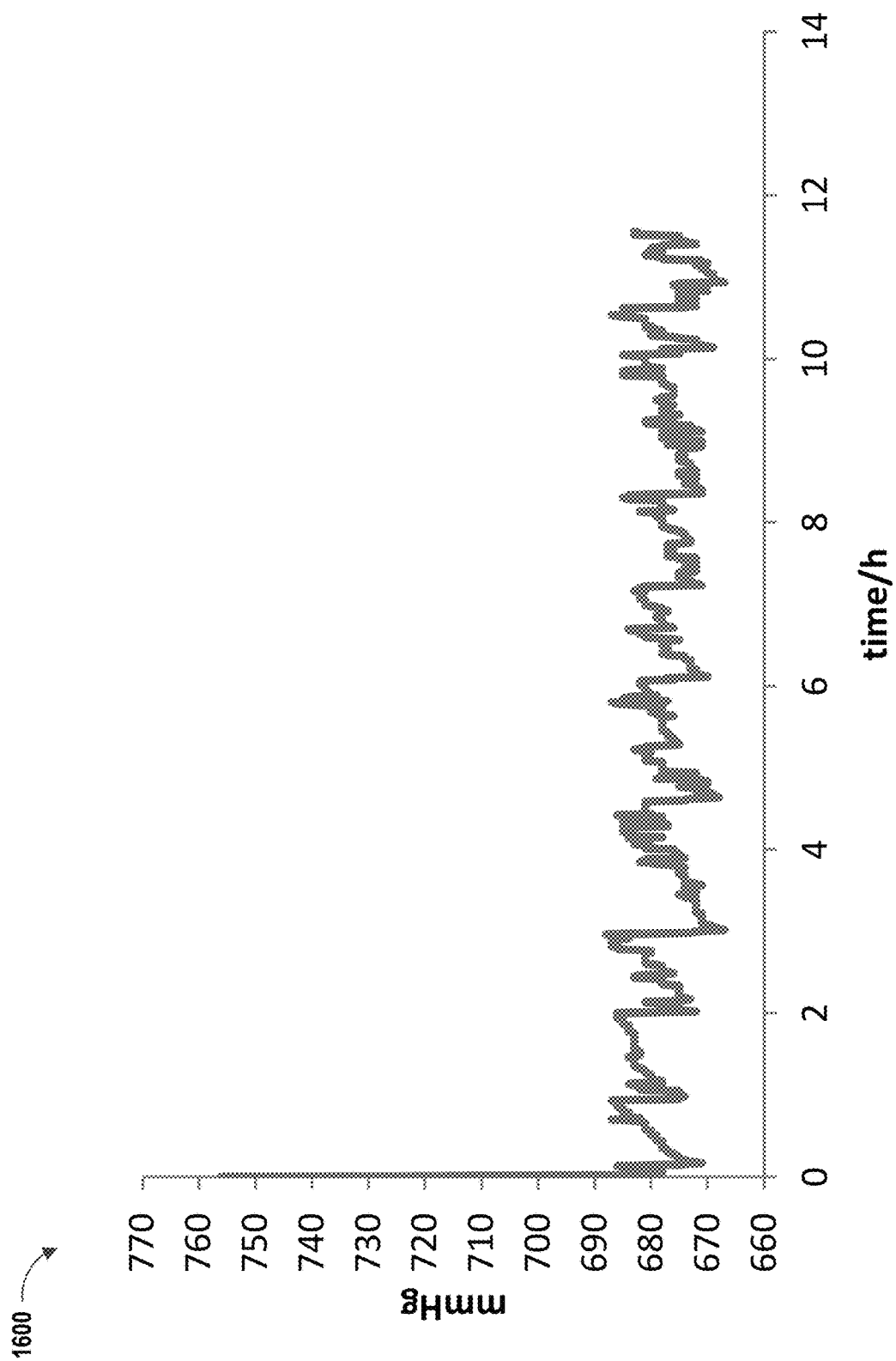
FIG. 16 provides a plot which illustrates how a magnitude of pressure measured by the pressure sensor can change over different wears by a patient according to some embodiments.
Figure 17:
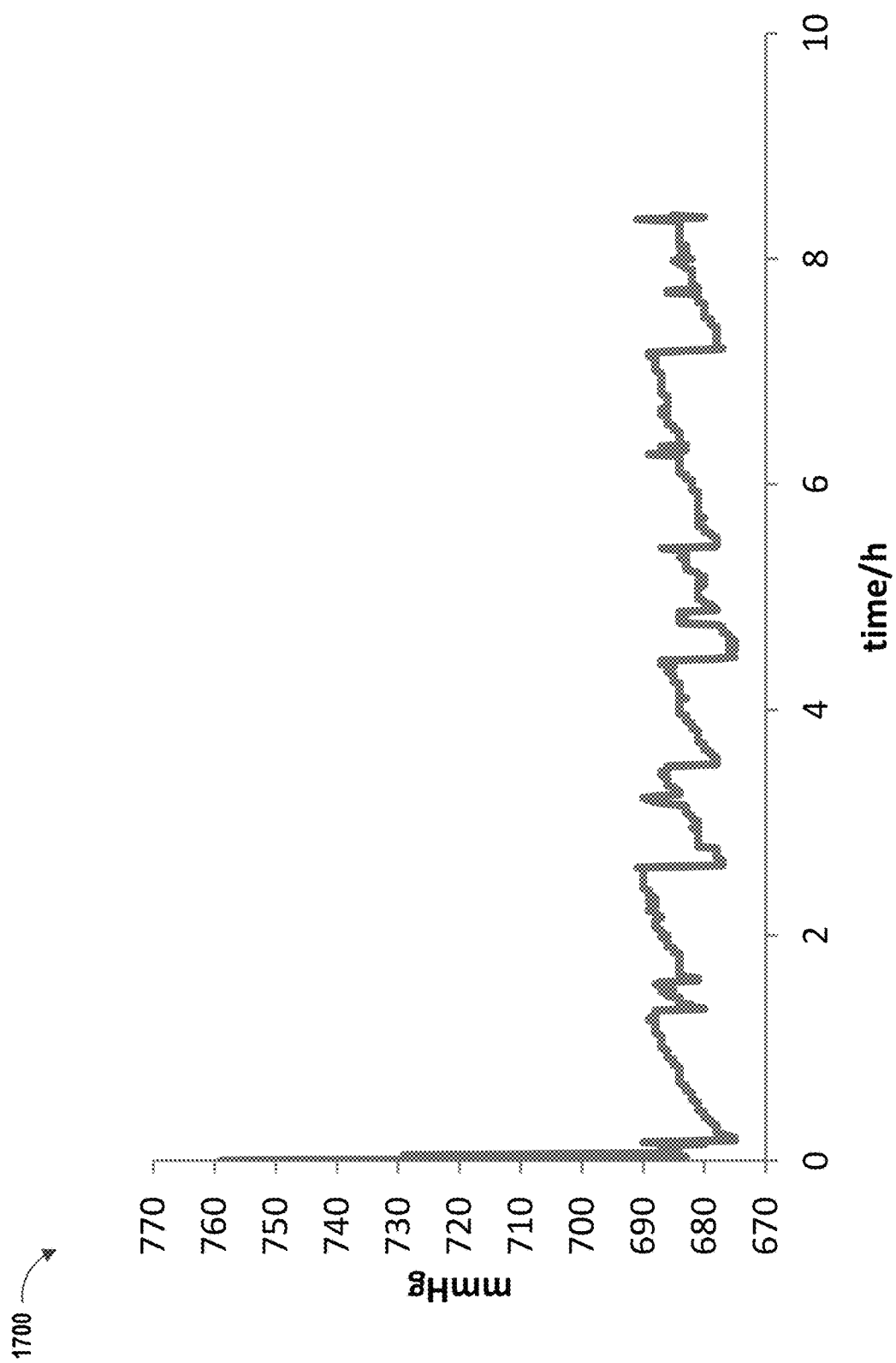
FIG. 17 provides a plot which illustrates how a magnitude of pressure measured by the pressure sensor can change over different wears by a patient according to some embodiments.

FIGS. 15-17 provide a plot 1500, a plot 1600, and a plot 1700 which illustrate how a magnitude of pressure measured by the pressure sensor 220 can change over different wears by a patient. A controller, such as the controller 210, can, for example, determine from the magnitude of pressure shown in the plot 1600 that the patient performed a high level of ambulation and determine from the magnitude of pressure shown in the plot 1700 that the patient performed a low level of ambulation.

Figure 24:
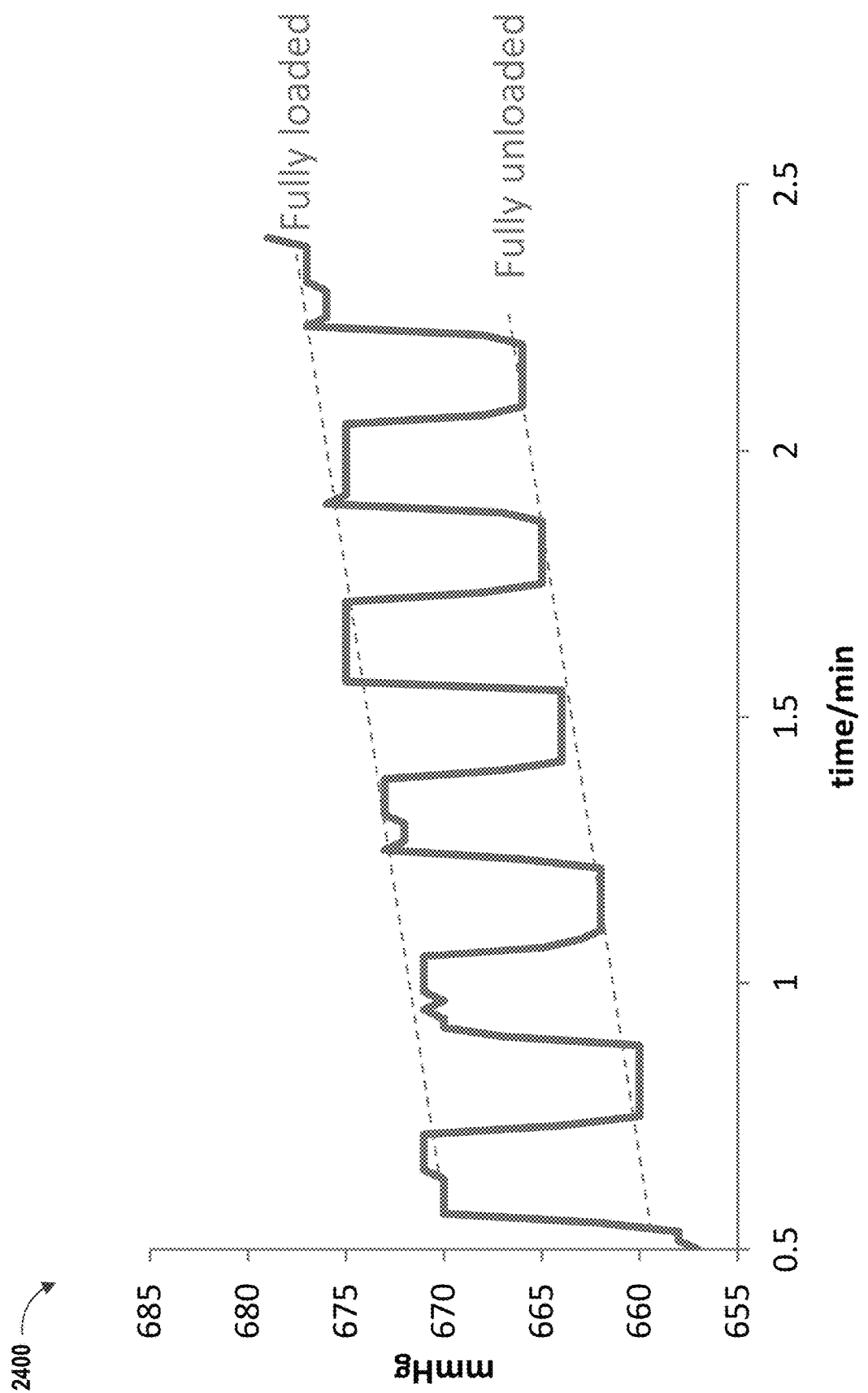
FIG. 24 provides a plot which illustrates how a magnitude of pressure can be used to determine an activity classification for a patient with a wound dressing positioned on his or her shoulder according to some embodiments.

While FIGS. 12-17 or any other embodiments disclosed herein may illustrate a constant negative pressure threshold over time (such as, a threshold represented by a horizontal line), in some examples, the negative pressure threshold can increase or decrease over time (see, for example, FIGS. 24-26). This change in threshold can be a result of a variety of factors, including but not limited to increases or decreases in negative pressure under the wound dressing resulting from, for instance, pressure leakages in the system that cause decreases in negative pressure.

Figure 18:
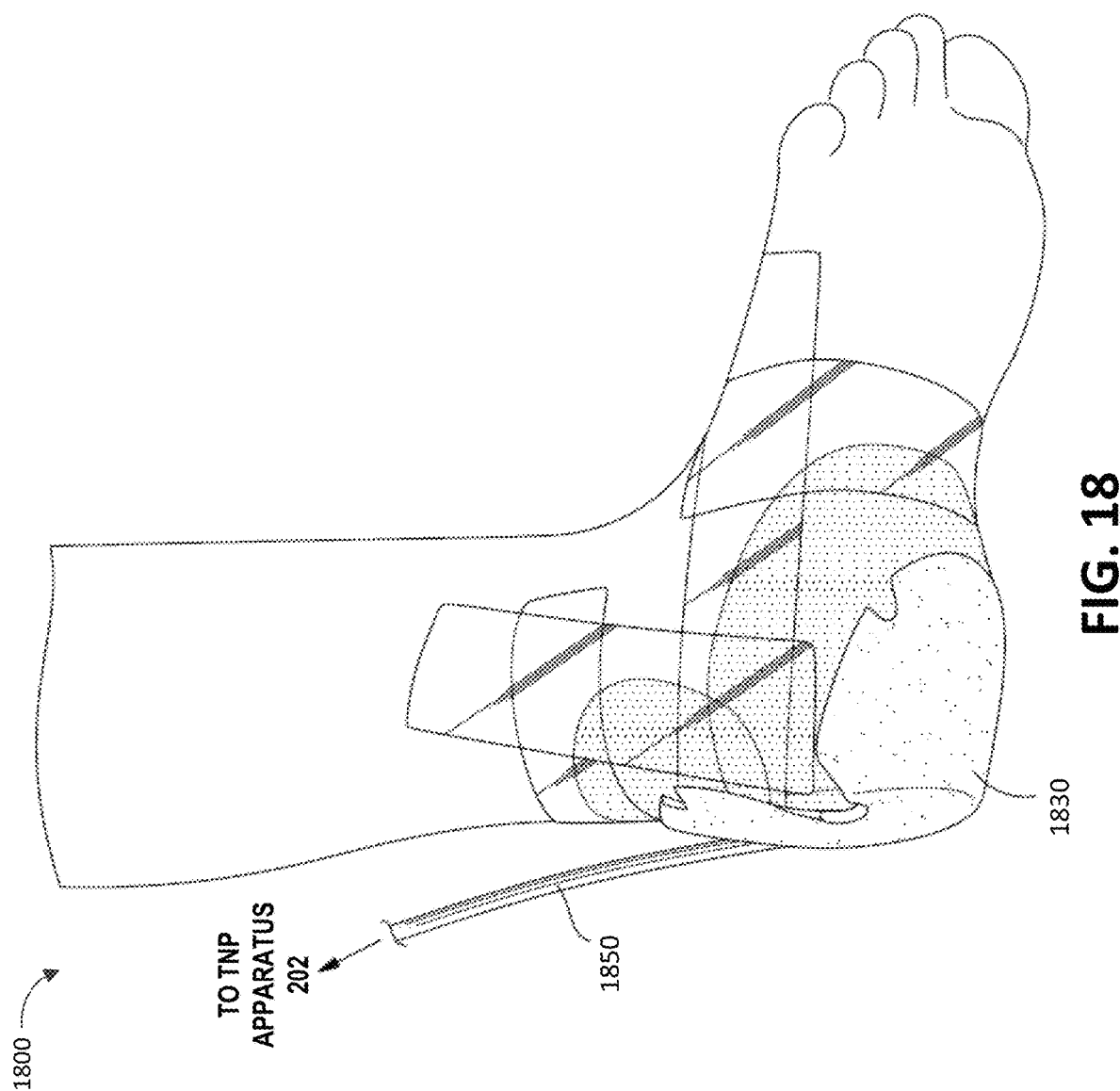
FIG. 18 illustrates a negative pressure wound therapy system in which a wound dressing is attached to a patient's heel and coupled to a TNP apparatus via a fluid flow path according to some embodiments.

FIG. 18 illustrates an example of a TNP system 1800 in which a wound dressing 1830, which can be one implementation of the wound dressing 330, is attached to a patient's heel and coupled to the TNP apparatus 202 via a fluid flow path 1850, which can be one implementation of the first fluid flow path 350. The TNP apparatus 202 can provide negative pressure wound therapy to the patient's heel via the fluid flow path 1850 and the wound dressing 1830, as well as monitor, track, and report movement by the patient while the TNP apparatus 202 maintains negative pressure under the wound dressing below a negative pressure threshold. The TNP apparatus 202 can be performing negative pressure therapy when negative pressure under the wound dressing is maintained below the negative pressure threshold.

Figure 19:
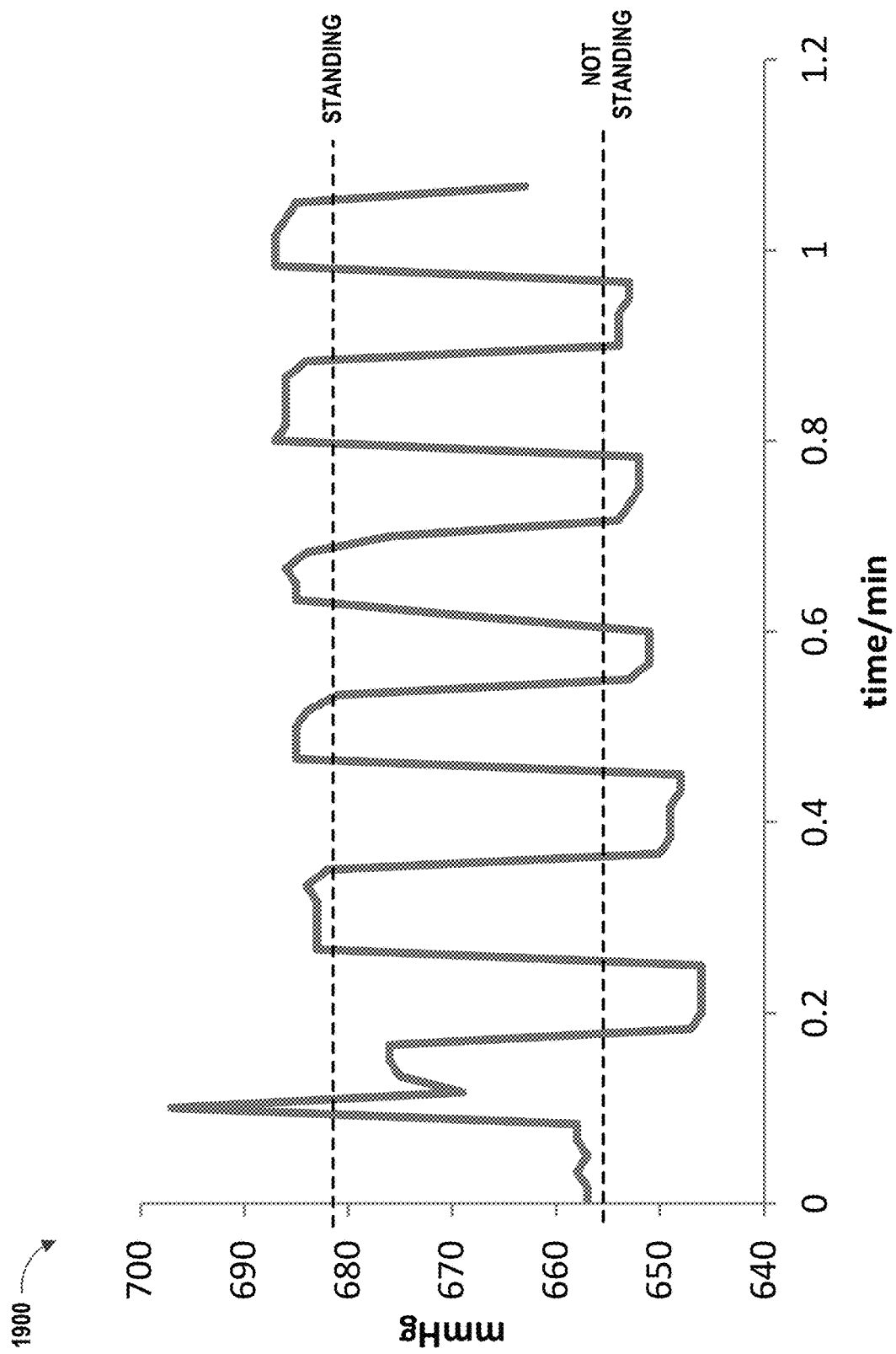
FIG. 19 provides a plot which illustrates how a magnitude of pressure measured by a pressure sensor can be used to determine an activity classification for a patient according to some embodiments.
Figure 20:
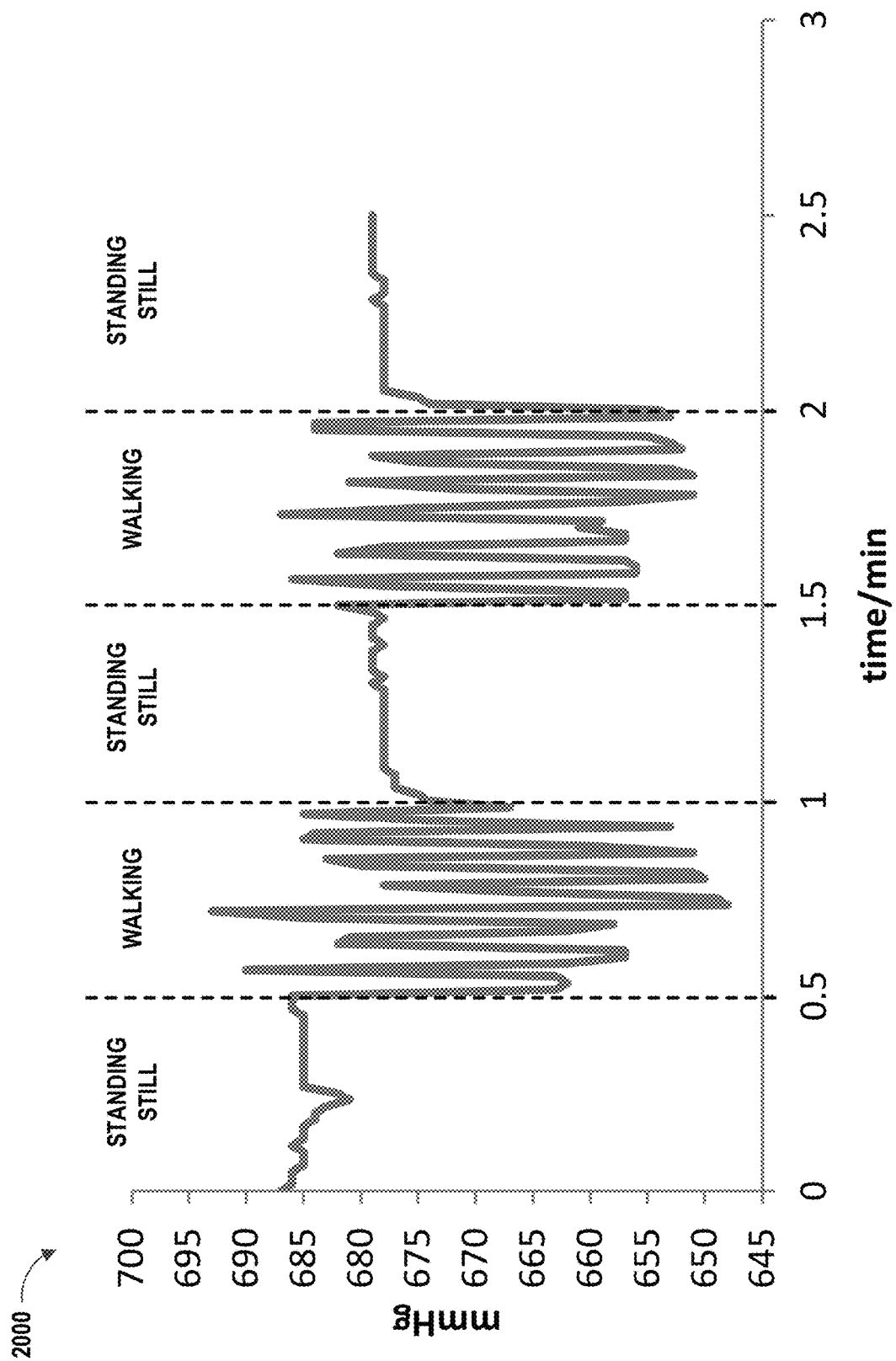
FIG. 20 provides a plot which illustrates how a magnitude or frequency of pressure measured by a pressure sensor can be used to determine an activity classification for a patient according to some embodiments.
Figure 21:
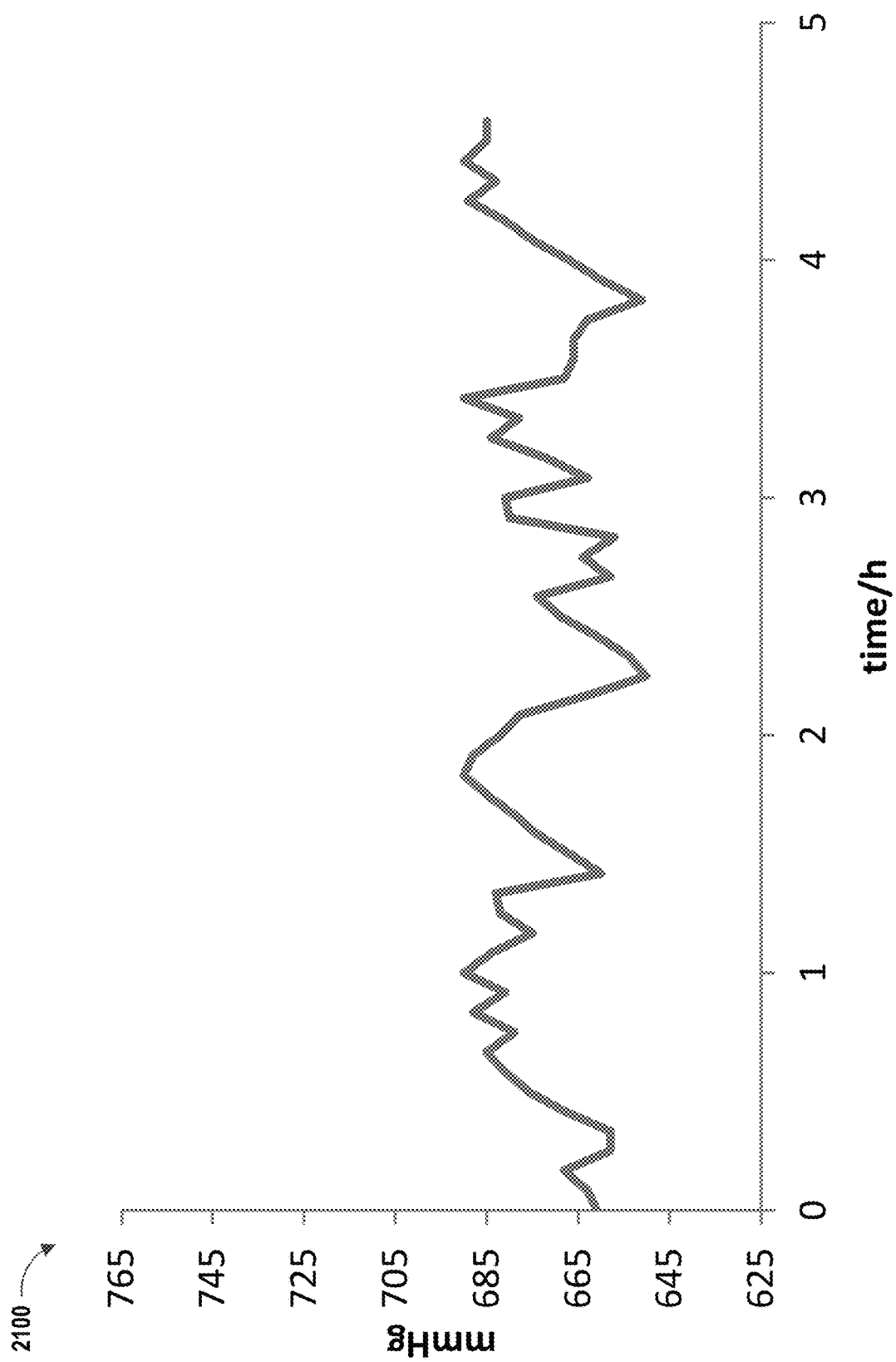
FIG. 21 provides a plot which illustrates how a magnitude of pressure measured by a pressure sensor can vary as a patient moves according to some embodiments.

FIGS. 19-21 illustrate example pressure variations over time in the TNP system 1800 of FIG. 18 while the TNP apparatus 202 maintains negative pressure under the wound dressing below a negative pressure threshold. The pressure in the TNP system can, for instance, vary by around 5 mmHg to 50 mmHg due to movement of the patient as illustrated.

FIG. 19 provides a plot 1900 which illustrates how a magnitude of pressure measured by the pressure sensor 220 can be used to determine an activity classification for a patient. In response to the magnitude of pressure rising above a standing threshold shown in the plot 1900 or remaining above the standing threshold shown in the plot 1900 for a period of time (for example, 1, 2, 3, 5, 7, 10, or 20 seconds), a controller, such as the controller 210, can determine that the patient is standing. In response to the magnitude of pressure falling below a not standing threshold shown in the plot 1900 or remaining below the not standing threshold shown in the plot 1900 for a period of time (for example, 1, 2, 3, 5, 7, 10, or 20 seconds), the controller 210 can determine that the patient is not standing. Not standing may mean, for example, that the patient is not applying weight to the heel to which the dressing is attached or that the heel is partially or fully off-loaded. The patient can transition from not standing to standing, for instance, when transitioning from lying in or sitting on a bed to standing up.

FIG. 20 provides a plot 2000 which illustrates how a magnitude or frequency of pressure measured by the pressure sensor 220 can be used to determine an activity classification for a patient.

A controller, such as the controller 210, can determine that the patient is standing still in various ways. For example, if the magnitude of pressure is at around a standing still threshold (e.g., about 685 mmHg), remains at around the standing still threshold for a period of time (for example, 1, 2, 3, 5, 7, 10, or 20 seconds), or varies a relatively minimal amount over time (as illustrated by a standing still period illustrated in the plot 2000), the controller 210 can determine that the patient is standing still. Similarly, the controller can determine that the patient is standing still based on peak-to-peak pressure values. For example, if the peak-to-peak value of the pressure pulses is approximately zero or relatively minimal, the controller can determine that the patient is not moving (e.g., is standing still).

Furthermore, in some embodiments, frequency of the pressure signal can be used in addition to or instead of changes in amplitude for determination of an activity classification. For example, as is shown in FIG. 20, the frequency of the detected pressure signal decreases or drops as the patient moves less or becomes more still. The frequency of the detected pressure signal can be compared to one or more frequency thresholds, which may be determined to detect that the patient is standing still.

A controller, such as the controller 210, can determine that the patient is walking in various ways. For example, if the magnitude of pressure is at around the standing threshold, remains at around the sitting threshold for a period of time (for example, 1, 2, 3, 5, 7, 10, or 20 seconds), or varies a relatively moderate amount (e.g., approximately 40 mmHg) over time as illustrated by a walking period illustrated in the plot 2000, the controller 210 can determine that the patient is walking. Similarly, the controller can determine that the patient is walking based on peak-to-peak pressure values. If the peak-to-peak value of the pressure pulses is approximately equal to the standing threshold minus a relatively moderate amount (e.g. 20, 30, 40, 50, or 60 mmHg), the controller can determine that the patient is moving (e.g., walking). For example, if the peak-to-peak pressure value is approximately 45 mmHg, the controller may determine that the patient is walking.

FIG. 21 provides a plot 2100 which illustrates how a magnitude of pressure measured by the pressure sensor 220 can vary as a patient moves.

The wound dressing 330 can be attached to a patient's heel, hip, shoulder, knee, torso, abdomen, or elbow and coupled to the TNP apparatus 202 via a fluid flow path, such as the first fluid flow path 350. The TNP apparatus 202 can provide negative pressure wound therapy to the patient's heel, elbow, shoulder, hip, knee, torso, or abdomen via the fluid flow path and the wound dressing 330, as well as monitor, track, and report movement by the patient while the TNP apparatus 202 maintains negative pressure under the wound dressing below a negative pressure threshold. The TNP apparatus 202 can be performing negative pressure therapy when negative pressure under the wound dressing is maintained below the negative pressure threshold. In some implementations, the TNP apparatus 202 can determine whether a patient is lying down, not lying down, or is changing positions while lying down according to the pressure variation in the TNP system. The threshold pressure in such a TNP system can, for instance, vary by around 5 mmHg to 50 mmHg due to such movement of the patient.

Figure 22:
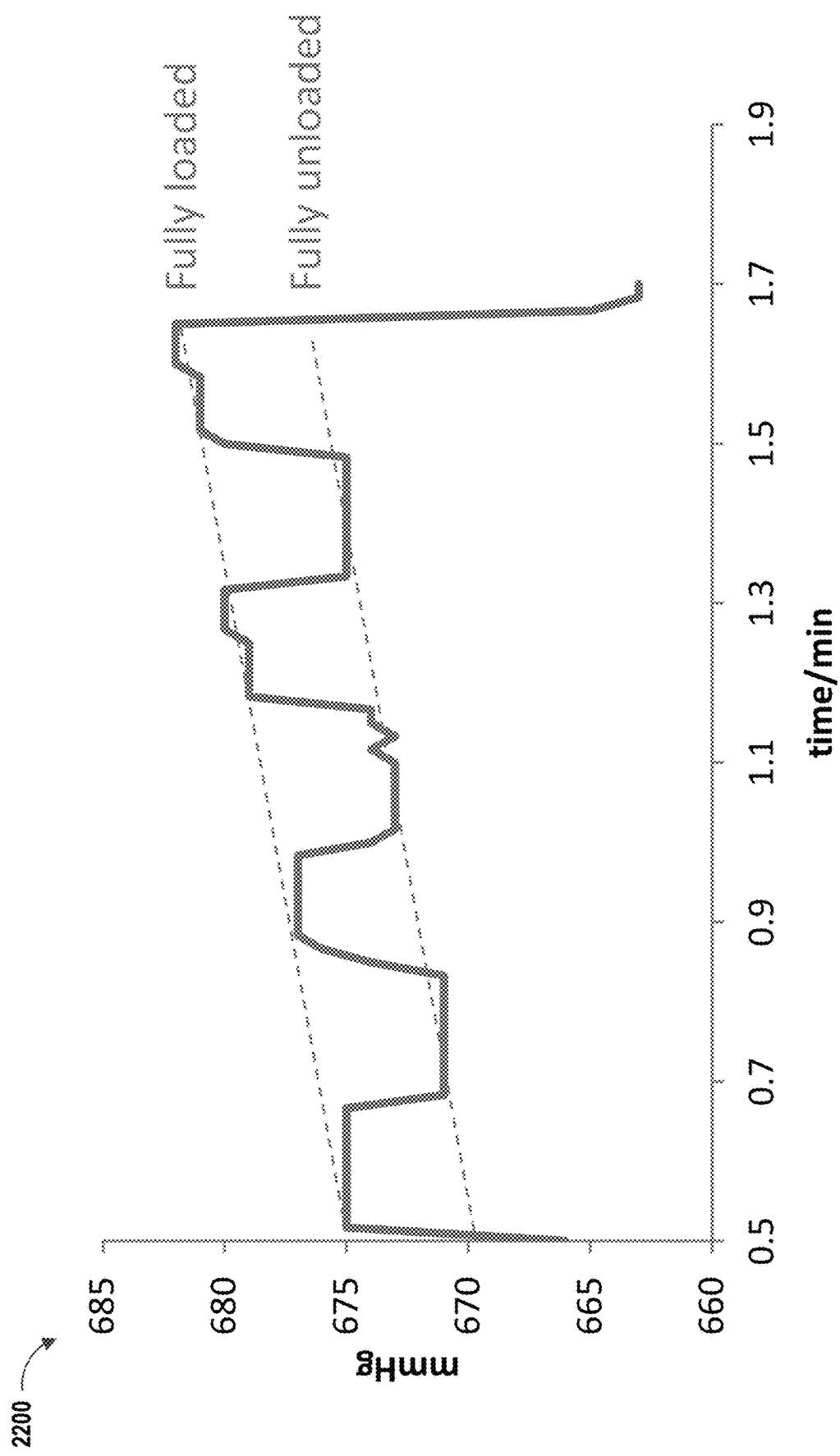
FIG. 22 provides a plot which illustrates how a magnitude of pressure can be used to determine an activity classification for a patient with a wound dressing positioned on his or her heel according to some embodiments.

FIG. 22 provides a plot 2200 which illustrates how a magnitude of pressure measured by the pressure sensor 220 can be used to determine an activity classification for a patient with a wound dressing positioned on his or her heel. For example, a magnitude of pressure can vary as a patient changes positions. The threshold pressure change can, for instance, vary about 5 mmHg when the dressing is positioned on the heel of the patient. In other cases, the threshold pressure can vary 1, 2, 3, 4, 5, 6, 7, 8, 9, 10 mmHg or any other suitable value.

As is illustrated, the magnitude of negative pressure decreases (or becomes more positive) when the heel is fully loaded, such as when the heel bears the patient's weight. Conversely, the magnitude of pressure increases (or becomes more negative) when the heel is fully unloaded, such as when the leg on which the dressing is positioned is raised. The plot 2200 can represent a sequence of pressure measurements taken while a laying patient raises the leg wearing the dressing (fully offloaded) for 10 seconds or another suitable period of time and then repositions the leg on the mattress (fully loaded) for 10 seconds or another suitable period of time. The pressure measurements can be taken, for example, every second or any other suitable frequency over a two minute duration or any other suitable duration. In some embodiments, monitoring the pressure over time can be used to monitor the orientation of a patient in the bed, such as, determining if the patient is moving his or her leg.

Figure 23:
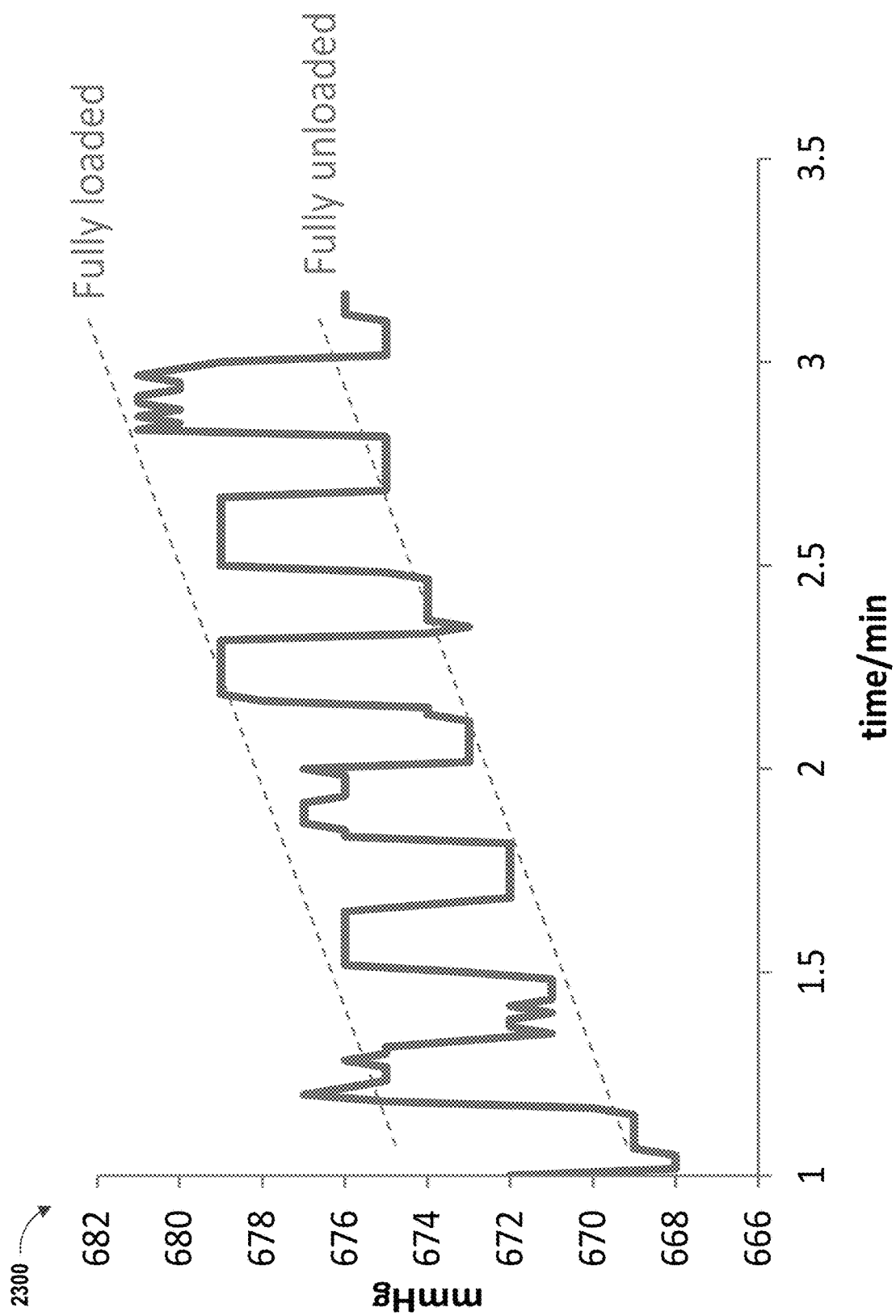
FIG. 23 provides a plot which illustrates how a magnitude of pressure can be used to determine an activity classification for a patient with a wound dressing positioned on his or her hip according to some embodiments.

FIG. 23 provides a plot 2300 which illustrates how a magnitude of pressure measured by the pressure sensor 220 can be used to determine an activity classification for a patient with a wound dressing positioned on his or her hip. For example, a magnitude of pressure can vary as a patient changes positions. The threshold pressure change can, for instance, vary about 6 mmHg when the dressing is positioned on the hip of the patient. In other cases, the threshold pressure can vary 1, 2, 3, 4, 5, 6, 7, 8, 9, 10 mmHg or any other suitable value.

As is illustrated, the magnitude of negative pressure decreases (or becomes more positive) when the hip is fully loaded, such as when the hip bears the patient's weight. Conversely, the magnitude of pressure increases (or becomes more negative) when the hip is fully unloaded, such as when the patient is not lying on the side on which the dressing is positioned. The plot 2300 can represent a sequence of pressure measurements taken while a laying patient transitions between lying on the side on which the dressing is positioned (fully loaded) for 10 seconds or any other suitable period of time to lying supine or prone (fully unloaded) for 10 seconds or any other suitable period of time. The pressure measurements can be taken, for example, every second or any other suitable frequency over a two minute duration or any other suitable duration. In some embodiments, monitoring the pressure over time can be used to monitor the orientation of a patient in the bed, such as, determining if the patient is turning.

FIG. 24 provides a plot 2400 which illustrates how a magnitude of pressure measured by the pressure sensor 220 can be used to determine an activity classification for a patient with a wound dressing positioned on his or her shoulder. For example, a magnitude of pressure can vary as a patient changes positions. The threshold pressure change can, for instance, vary about 10 mmHg when the dressing is positioned on the shoulder of the patient. In other cases, the threshold pressure can vary 1, 2, 3, 4, 5, 6, 7, 8, 9, 10 mmHg or any other suitable value.

As is illustrated, the magnitude of negative pressure decreases (or becomes more positive) when the shoulder is fully loaded, such as when the shoulder bears the patient's weight. Conversely, the magnitude of pressure increases (or becomes more negative) when the shoulder is fully unloaded, such as when the patient is not lying on the side on which the dressing is positioned. The plot 2400 can represent a sequence of pressure measurements taken while a laying patient transitions between lying on the side on which the dressing is positioned (fully loaded) for 10 seconds or any other suitable period of time to lying supine or prone (fully unloaded) for 10 seconds or any other suitable period of time. The pressure measurements can be taken, for example, every second or any other suitable frequency over a two minute duration or any other suitable duration. In some embodiments, monitoring the pressure over time can be used to monitor the orientation of a patient in the bed, such as, determining if the patient is turning.

In some embodiments, in response to a change in magnitude of pressure, a controller, such as the controller 210, can be configured to determine that a patient is changing positions while lying down or in another position. For example, the threshold pressure in such a TNP system can, for instance, vary by around 5 mmHg to 50 mmHg (or any other suitable value) due to such movement of the patient. In response to the magnitude of pressure varying between the fully loaded threshold and fully unloaded threshold (as shown, for example in FIGS. 22-24), the controller 210 can determine that the patient is changing positions (such as turning over, laying on one's side, sitting up, bending knee or elbow, etc.). In some instances, the controller 210 is further configured to output an indication that the individual is changing positions while lying in response to the change in the magnitude of pressure satisfying a threshold pressure change.

In some implementations, a controller, such as the controller 210, is configured to detect a duration of time during which the patient has not changed positions while lying down or in another position. Detection of patient movement can be used to detect physiological condition(s), such as detecting patient breathing, heart rate, pulse rate, consciousness, and the like, or prevent or decrease the likelihood of injury, development of pressure ulcers (also known as pressure sores or bedsores), loss of consciousness, and the like. Detection of a patient breathing can be performed using any of the approaches described herein when the dressing is positioned on the patient's torso, chest, wrist, neck or any other area where breathing can be detected. In some cases, the dressing can be connected to a custom interface designed to detect patient's breathing, such as strap (for example, a circumferential inflatable strap) configured to be worn around the chest, an attachment (for example, a rigid hemisphere configured) to be placed over a prominent pulse area, such as the wrist, neck, etc. Detection of a patient's heart rate or pulse rate can be performed using any of the approaches described herein (for example, similarly to the detection of patient's breathing). In some embodiments, the change in the detected pressure as a result of the patient breathing or pulsing blood can be associated with the respiration rate, heart rate, or pulse rate.

For instance, if the magnitude of pressure measured by the pressure sensor 220 falls below a fully unloaded threshold for a period of time (for example, 10 minutes, 15 minutes, 30 minutes, 1 hour, 2 hours, 3 hours, 5 hours, 8 hours), the indication that the individual has not changed positions can be associated with at least one of development of a pressure ulcer, development of an injury, or loss of consciousness. In response, the controller can trigger an alarm, notify a caregiver, begin to take more frequent pressure measurements, or otherwise determine that a patient may need medical attention.

Physiological characteristics can be determined by the controller in a variety of ways. For instance, in response to a magnitude of pressure varying a relatively moderate amount (for example, less than 1, 2, 3, or 4 mmHg or any other suitable pressure) over time (for example, 1, 2, 3, 5, 7, 10, or 20 seconds or any other suitable time duration), a controller, such as the controller 210, can detect physiological characteristics (such as respiration rate, pulse, heart rate) of the patient based on the change in magnitude over time. For example, the controller 210 can be configured to detect a patient's respiration rate or breathing when a dressing is applied to an area of the body, such as the patient's torso. Similarly, the controller 210 can be configured to detect a patient's heart rate or pulse when a dressing is applied to an area of the body, such as a patient's heel, hip, shoulder, knee, torso, abdomen, or elbow.

In some examples, one or more or sensors can be utilized in conjunction with a pressure sensor to determine physiological characteristics of a patient. For instance, a chest strap can be configured to measure respiration, a neck or wrist strap can be configured to measure pulse, and a heart rate monitor can be configured to measure heart rate. The physiological characteristics determined by the pressure sensor and the other sensor(s) can be compared to determine an estimated accuracy level. If the estimated accuracy level meets or satisfies a threshold, the physiological characteristics can be output to a user.

In some examples, the magnitude of pressure can be used by a controller of a TNP apparatus to calculate, estimate, monitor, track, or report physiological characteristics (such as respiration rate, pulse, heart rate) of the patient. Detection can be performed, for example, in response to rhythmic changes in the magnitude of pressure.

In yet another example, the wound dressing 330 can be attached to a patient's elbow and coupled to the TNP apparatus 202 via a fluid flow path, such as the first fluid flow path 350. The TNP apparatus 202 can provide negative pressure wound therapy to the patient's elbow via the fluid flow path and the wound dressing 330, as well as monitor, track, and report movement by the patient while the TNP apparatus 202 maintains negative pressure under the wound dressing below a negative pressure threshold. The TNP apparatus 202 can be performing negative pressure therapy when negative pressure under the wound dressing is maintained below the negative pressure threshold. In some implementations, the TNP apparatus 202 can determine whether a patient is bending the elbow versus extending the elbow according to the pressure variation in the TNP system. The pressure in such a TNP system can, for instance, vary by around 5 mmHg to 50 mmHg due to such movement of the patient. The TNP apparatus 202 can thus be used to assist in prevention of pressure ulcers, such as from chair arms.

In some implementations, the geometry of a TNP system, such as a geometry of one or more of the TNP apparatus 202, the fluid flow path 350, and the wound dressing 330, can be modified or designed to amplify a detected pressure change. The geometry can, for example, be increased by increasing the volume change, and therefore pressure change, between different limb positions.

In some implementations, a dressing other than a wound dressing (for example, a dressing not used for treating a wound that has no perforations or absorbency and may be a three dimensional space) can be used with the embodiments disclosed herein. The TNP system could thus function as a movement detector without also performing negative wound pressure therapy.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An apparatus for applying negative pressure to a wound, comprising: a wound dressing comprising a wound cover configured to be positioned over the wound of a user; a fluid flow path in communication with the wound dressing, the fluid flow path comprising a lumen; a negative pressure source configured to couple via the fluid flow path to the wound dressing and provide negative pressure to the wound dressing; a sensor configured to monitor a magnitude of pressure in the fluid flow path generated by the negative pressure source; and a controller programmed to: determine an activity classification based on a change in the magnitude of pressure over time that is above a threshold pressure change value while the negative pressure source maintains the magnitude of pressure in the fluid flow path below a negative pressure threshold, the activity classification being indicative of a type of activity engaged in by an individual while wearing the wound dressing, and output an indication of the activity classification.

2. The apparatus of claim 1, wherein the activity classification comprises one or more of breathing, changing positions while lying, sitting, walking, standing, jumping, traversing stairs, leg extending, leg bending, and performing chair squats.

3. The apparatus of claim 1, wherein the wound dressing is configured to be positioned on one or more of a knee, a heel, an elbow, a shoulder, a hip, a torso, or an abdomen of the individual.

4. The apparatus of claim 1, wherein the controller is further programmed to: compare the activity classification to an assigned classification associated with the individual; and output an indication of whether the activity classification matches the assigned classification.

5. The apparatus of claim 4, wherein the controller is further programmed to activate or deactivate the negative pressure source in response to the activity classification matching the assigned classification.

6. The apparatus of claim 1, further comprising a user interface configured to receive the activity classification as a user input to the user interface.

7. The apparatus of claim 1, wherein the activity classification is responsive to the change in the magnitude of pressure over a duration of at least 1 second, 10 seconds, 30 seconds, 1 minute, or 5 minutes.

8. The apparatus of claim 1, wherein the controller is further programmed to store, in a memory device, the indication of the activity classification in association with usage data reflecting usage of the negative pressure source during a corresponding time period.

9. The apparatus of claim 1, wherein the fluid flow path comprises at least one lumen.

10. The apparatus of claim 1, wherein the sensor is configured to monitor the pressure at at least one of the wound dressing, a lumen or more than one lumen of the fluid flow path, or an inlet of the negative pressure source.

11. The apparatus of claim 1, further comprising a canister configured to be in fluidic communication with the wound dressing and the negative pressure source via the fluid flow path, the canister being configured to collect exudate aspirated from the wound.

12. The apparatus of claim 1, wherein the negative pressure source is configured to supply negative pressure when the magnitude of pressure is maintained below the negative pressure threshold.

13. The apparatus of claim 1, wherein the controller is programmed to output an indication that the individual is changing positions while lying in response to the change in the magnitude of pressure satisfying a threshold pressure change.

14. The apparatus of claim 13, wherein:
the threshold pressure change is about 5 mmHg when the wound dressing is configured to be positioned on the heel;
the threshold pressure change is about 6 mmHg when the wound dressing is configured to be positioned on the hip; and
the threshold pressure change is about 10 mmHg when the wound dressing is configured to be positioned on the shoulder.

15. The apparatus of claim 1, wherein the controller is further programmed to detect a duration of time during which the individual has not changed positions while lying and output another indication in response to the detected duration satisfying a threshold duration.

16. The apparatus of claim 15, wherein the another indication that the individual has not changed positions is associated with at least one of development of a pressure ulcer, development of an injury, or loss of consciousness.

17. The apparatus of claim 1, wherein the controller is further programmed to determine and provide indication of breathing when the wound dressing is applied to the torso.

18. The apparatus of claim 1, wherein the controller is further programmed to detect and provide indication of at least one of a heart rate or a pulse rate based on the change in the magnitude of pressure over time.

19. The apparatus of claim 1, wherein the controller is further programmed to determine the activity classification based on a peak-to-peak change in the magnitude of pressure over time.

20. A method of operating a negative pressure wound therapy apparatus comprising:
operating a negative pressure source fluidically coupled via a fluid flow path to a wound dressing positioned over a wound of a patient;
monitoring, via a sensor, a magnitude of pressure in the fluid flow path;
determining, by a controller, an activity classification based on a change in the magnitude of pressure over time that is above a threshold pressure change value while the negative pressure source maintains the magnitude of pressure in the fluid flow path below a negative pressure threshold, the activity classification being indicative of a type of activity engaged in by the patient while wearing the wound dressing, and
outputting, by the controller, an indication of the activity classification;
wherein:
the threshold pressure change value is a first value when the wound dressing is positioned on a first position of a user;

the threshold pressure change value is a second value when the wound dressing is positioned on a second position of a user;

the first position is different than the second position; and the first value is different than the second value.

21. An apparatus for applying negative pressure to a wound, comprising: a wound dressing; a negative pressure source configured to couple via a fluid flow path to the wound dressing and provide negative pressure to the wound dressing; a sensor positioned to measure pressure at or near the wound dressing configured to collect data; and a controller programmed to: determine an activity classification based on a change in the magnitude of pressure over time that is above a threshold pressure change value, and output an indication of the activity classification wherein: the threshold pressure change value is a first value when the wound dressing is positioned on a first position of a user; the threshold pressure change value is a second value when the wound dressing is positioned on a second position of a user; the first position is different than the second position; and the first value is different than the second value.

* * * * *